United States Patent …

(12) United States Patent
Martignetti et al.

(10) Patent No.: US 9,822,418 B2
(45) Date of Patent: Nov. 21, 2017

(54) MUTATIONS IN PDGFRB AND NOTCH3 AS CAUSES OF AUTOSOMAL DOMINANT INFANTILE MYOFIBROMATOSIS

(71) Applicants: ICAHN SCHOOL OF MEDICINE AT MOUNT SINAI, New York, NY (US); CHILDREN'S HOSPITAL OF PHILADELPHIA, Philadelphia, PA (US)

(72) Inventors: John A. Martignetti, New York, NY (US); Hakon Hakonarson, Malvern, PA (US); Lifeng Tian, Philadelphia, PA (US)

(73) Assignees: ICAHN SCHOOL OF MEDICINE AT MOUNT SINAI, New York, NY (US); THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 0 days.

(21) Appl. No.: 14/786,425

(22) PCT Filed: Apr. 22, 2014

(86) PCT No.: PCT/US2014/035000
§ 371 (c)(1),
(2) Date: Oct. 22, 2015

(87) PCT Pub. No.: WO2014/176259
PCT Pub. Date: Oct. 30, 2014

(65) Prior Publication Data
US 2016/0083799 A1    Mar. 24, 2016

Related U.S. Application Data

(60) Provisional application No. 61/814,439, filed on Apr. 22, 2013.

(51) Int. Cl.
C12Q 1/68     (2006.01)
A61K 31/506   (2006.01)
(Continued)

(52) U.S. Cl.
CPC .......... *C12Q 1/6886* (2013.01); *A61K 31/506* (2013.01); *A61K 45/06* (2013.01);
(Continued)

(58) Field of Classification Search
None
See application file for complete search history.

(56) References Cited

U.S. PATENT DOCUMENTS

2015/0316552 A1* 11/2015 Cain ................ G01N 33/57484
424/139.1

OTHER PUBLICATIONS

Andrae et al., "Role of platelet-derived growth factors in physiology and medicine," *Genes Dev.*, 22(10):1276-1312, 2008.
(Continued)

*Primary Examiner* — Michael Barker
(74) *Attorney, Agent, or Firm* — Parker Highlander PLLC

(57) ABSTRACT

This invention relates to a method of diagnosing a subject as having and/or being a carrier for infantile myofibromatosis. This method involves providing an isolated biological sample from a subject; contacting the sample with one or more reagents suitable for detecting the presence or absence of one or more mutations in PDGFRB and/or NOTCH3; detecting, in the sample, the presence or absence of the one or more mutations in PDGFRB and/or NOTCH3 based on said contacting; and diagnosing the subject as having and/or being a carrier for infantile myofibromatosis based on said detecting, where the presence of the one or more mutations in PDGFRB and/or NOTCH3 indicates the subject has a mutation that causes infantile myofibromatosis. Also disclosed is a method of treating a subject having infantile
(Continued)

myofibromatosis and a method of preventing or treating symptoms associated with infantile myofibromatosis.

23 Claims, 7 Drawing Sheets

(51) Int. Cl.
   *A61K 45/06* (2006.01)
   *A61N 5/00* (2006.01)
   *C12Q 1/66* (2006.01)
(52) U.S. Cl.
   CPC ............. *A61N 5/00* (2013.01); *C12Q 1/6883* (2013.01); *C12Q 2600/156* (2013.01)

(56) References Cited

OTHER PUBLICATIONS

Apasricio-Gallego et al., "New insights into molecular mechanisms of sunitinib-associated side effects," *Mol. Cancer Ther.*, 10(12):2215-2223, 2011.
Arts et al., "PDGFRB gain-of-function mutations in sporadic infantile myofibromatosis," *Hum. Mol. Genet.*, 26(10):1801-1810, 2017.
Arts et al., "PDGFRB mutants found in patients with familial infantile myofibromatosis or overgrowth syndrome are oncogenic and sensitive to imatinib," *Oncogene*, 35(25):3239-48, 2016.
Cheung et al., "A recurrent PDGFRB mutation causes familial infantile myofibromatosis," *Am. J. Hum. Genet.*, 92(6):996-1000, 2013.
Extended European Search Report issued in European Patent Application No. 14787679.1, dated Dec. 16, 2016.
Fouillade et al., "Activating NOTCH3 mutation in a patient with Small-vessel-disease of the brain," *Hum. Mutat.*, 29(3):452, 2008.
Franzese et al., "Infantile myofibromatosis: unusual diagnosis in an older child," *International Journal of Pediatric Otorhinolaryngology*, 69(6):865-868, 2005.
Ikediobi et al., "Infantile myofibromatosis: support for autosomal dominant inheritance," *J. Am. Acad. Dermatol.*, 49(2 Suppl. Case Reports):S148-5150, 2003.
Jennings et al., "Infantile myofibromatosis. Evidence for an autosomal-dominant disorder," *Am. J. Surg. Pathol.*, 8(7):529-538, 1984.
Jin et al., "Notch signaling regulates platelet-derived growth factor receptor-beta expression in vascular smooth muscle cells," *Circ. Res.*, 102(12):1483-1491, 2008.
Joutel et al.,"Notch3 mutations in CADASIL, a hereditary adult-onset condition causing stroke and dementia," *Nature*, 383(6602):707-710, 1996.
Lee, "Mutations in PDGFRB and NOTCH3 are the first genetic causes identified for autosomal dominant infantile myofibromatosis," *Clinical Genetics*, 84(4):340-341, 2013.
Lepelletier et al., "Heterozygous Pdgfrb Mutation in a Three-generation Family with Autosomal Dominant Infantile Myofibromatosis," *Acta Derm. Venereol.*, DOI: 10.2340/00015555-2671, 2017.
Martignetti et al., "Mutations in PDGFRB cause autosomal-dominant infantile myofibromatosis," *Am. J. Hum. Genet.*, 92(6):1001-1007, 2013.
Muchy et al., "Case report: rapid and durable response to PDGFR targeted therapy in a child with refractory multiple infantile myofibromatosis and a heterozygous geiniline mutation of the PDGFRB gene," *BMC Cancer*, 17(1):119, 2017.
Murray et al., "The spectrum of infantile myofibromatosis includes both non-penetrance and adult recurrence," *Eur. J. Med. Genet.*, 60(7):353-358, 2017.
Narchi, "Four half-siblings with infantile myofibromatosis: a case for autosomal-recessive inheritance," *Clinical Genetics*, 59(2):134-135, 2001.
Nicolas et al., "Mutation of the PDGFRB gene as a cause of idiopathic basal ganglia calcification," *Neurology*, 80(2):181-7, 2013.
PCT International Search Report and Written Opinion issued in International Application No. PCT/US2014/035000, dated Oct. 1, 2014.
Smith et al., "Infantile myofibromatosis: Two families supporting autosomal dominant inheritance," *Australian Journal of Dermatology*, 52(3):214-217, 2011.
Vanlandewijck et al., "Functional Characterization of Germline Mutations in PDGFB and PDGFRB in Primary Familial Brain Calcification," *PLOS ONE*, 10(11):e0143407, DOI: 10.1371/journal.pone.0143407, eCollection, 2015.
Zand et al.," Autosomal dominant inheritance of infantile myofibromatosis," *Am. J. Med. Genet. Part A*, 126A(3):261-266, 2004.

* cited by examiner

FIGs. 2A-B

| Gene (MIM) | Genomic Location (hg19) RefSeq | Exon | Famiy | cDNA | Protein | MAF in 1000 genomes project or ESP6500SI |
|---|---|---|---|---|---|---|
| PDGFRB (173410) | chr5:149503858 NM 002609.3 | 14 | IM1 | c.1978C>A | Pro660Thr | 0.000077 |
| PDGFRB (173410) | chr5: 149505134 NM 002609.3 | 12 | IM2-8 | c.1681C>T | Arg561Cys | - |
| NOTCH3 (600276) | chr19: 15285059 NM 000435.2 | 25 | IM9 | c.4556T>C | Leu1519Pro | - |

MUTATIONS IN PDGFRB AND NOTCH3 AS CAUSES OF AUTOSOMAL DOMINANT INFANTILE MYOFIBROMATOSIS

The application is a national phase application under 35 U.S.C §371 of International Application No. PCT/US2014/035000, filed Apr. 22, 2014, which claims the priority benefit of U.S. Provisional Application Ser. No. 61/814,439, filed Apr. 22, 2013. The entire contents of the above-reference disclosures are specifically incorporated herein by reference.

FIELD OF THE INVENTION

The present invention relates to methods of diagnosis, treatment, and prevention of infantile myofibromatosis.

BACKGROUND OF THE INVENTION

Infantile myofibromatosis (MIM 228550) ("IM") is one of the most common proliferative fibrous tumors of infancy and childhood. First described by Williams et al., "Congenital Fibrosarcoma: Report of a Case in a Newborn Infant," *AMA Arch. Pathl.* 51:548-552 (1951) and Stout (Stout, "Juvenile Fibromatoses," *Cancer* 7:953-978 (1954)), IM was further sub-categorized by others into solitary, multiple or generalized forms and shown to affect the skin, muscle, bone, and viscera (Kauffman et al., "Congenital Mesenchymal Tumors," *Cancer* 18:460-476 (1965)). The term "infantile myofibromatosis" was recommended based on the fact that the cells have features of both differentiated fibroblasts and smooth muscle cells (myofibroblasts) (Chung et al., "Infantile Myofibromatosis," *Cancer* 48:1807-1818 (1981)). Soft tissue lesions usually arise during childhood but can arise at any time during life and, intriguingly, can regress spontaneously. On the other hand, visceral lesions are associated with high morbidity and mortality (Wiswell et al., "Infantile Myofibromatosis: The Most Common Fibrous Tumor of Infancy," *J. Pediatr. Surg.* 23:315-318 (1988)). The mechanism(s) underlying tumor growth and regression are not known. Some have suggested tumor growth to be linked to angiogenic stimulation and regression (Leaute-Labreze et al., "A Self-healing Generalized Infantile Myofibromatosis with Elevated Urinary bFGF," *Ped. Derm.* 18:305-307 (2001)). Indeed, in a single case report, regression of an intracardiac IM was achieved through use of interferon alpha-2b (Auriti et al., "Remission of Infantile Generalized Myofibromatosis After Interferon Alpha Therapy," *J. Pediatr. Hematol. Oncol.* 30:179-181 (2008)).

The genetic etiology of IM is unknown and both autosomal recessive ("AR") and dominant ("AD") patterns of inheritance have been reported. Consanguinity in a number of pedigrees has been interpreted to be in accord with an AR pattern of inheritance (Baird et al., "Congenital Generalized Fibromatosis: An Autosomal Recessive Condition?" *Clin. Genet.* 9:488-494 (1976); Salamah et al., "Infantile Myofibromatosis," *J. Pediatr. Surg.* 23:975-977 (1988); Narchi, "Four Half-Siblings with Infantile Myofibromatosis: A Case for AutosomalRecessive Inheritance," *Clin. Genet.* 59:134-135 (2001)). A large number of pedigrees, where affected individuals are identified across generations, are consistent with IM being an AD disease (Bartlett et al., "Multiple Congenital Neoplasms of Soft Tissues: Report of 4 Cases in 1 Family," *Cancer* 14:913-920 (1960); Pfluger et al., "Kongenitale Polyfibromatose: Klinische and Genetische Untersuchungen," *Wiener Klinishe Wochenshrift* 88:92-94 (1976); Jennings et al., "Infantile Myofibromatosis: Evidence for an Autosomal-dominant Disorder," *Am. J. Surg. Pathol.* 8:529-538 (1984); Ikediobi et al., "Infantile Myofibromatosis: Support for Autosomal Dominant Inheritance," *J. Am. Acad. Dermatol.* 49:S148-150 (2003); Zand et al., "Autosomal Dominant Inheritance of Infantile Myofibromatosis," *Am. J. Med. Genet. A.* 126:261-266 (2004); de Montpréville et al., "Endocardial Location of Familial Myofibromatosis Revealed by Cerebral Embolization: Cardiac Counterpart of the Frequent Intravascular Growth of the Disease?" *Virchows Arch.* 444:300-303 (2004); Smith et al., "Infantile Myofibromatosis: Two Families Supporting Autosomal Dominant Inheritance," *Australas J. Dermatol.* 52:214-217 (2011); Kulkarni et al., "Infantile Myofibromatosis: Report on a Family with Autosomal Dominant Inheritance and Variable Penetrance," *J. Pediatr. Surg.* 47:2312-2315 (2012)).

The present invention is directed to overcoming deficiencies in the art.

SUMMARY OF THE INVENTION

One aspect of the present invention relates to a method of diagnosing a subject as having and/or being a carrier for infantile myofibromatosis. This method involves providing an isolated biological sample from a subject; contacting the sample with one or more reagents suitable for detecting the presence or absence of one or more mutations in PDGFRB and/or NOTCH3; detecting, in the sample, the presence or absence of the one or more mutations in PDGFRB and/or NOTCH3 based on said contacting; and diagnosing the subject as having and/or being a carrier for infantile myofibromatosis based on said detecting, where the presence of the one or more mutations in PDGFRB and/or NOTCH3 indicates the subject has a mutation that causes infantile myofibromatosis.

Another aspect of the present invention relates to a method of treating a subject having infantile myofibromatosis. This method involves selecting a subject having one or more mutations in PDGFRB and/or NOTCH3 and administering a therapy suitable for treating infantile myofibromatosis to the selected subject.

A further aspect of the present invention relates to a method of preventing or treating symptoms associated with infantile myofibromatosis. This method involves selecting a subject having one or more mutations in PDGFRB and/or NOTCH3 and administering to the selected subject an agent that modulates PDGFRB and/or NOTCH3 gene expression and/or PDGFRB and/or NOTCH3 encoded protein activity under conditions effective to prevent or treat symptoms associated with infantile myofibromatosis in the subject.

Another aspect of the present invention relates to a method of diagnosing a subject as having and/or being a carrier for infantile myofibromatosis. This method involves providing an isolated biological sample from a subject. The sample is contacted with one or more reagents suitable for detecting PDGFRB and/or NOTCH3 RNA and/or protein levels. Levels of PDGFRB and/or NOTCH3 RNA and/or protein are detected in the sample based on said contacting. The subject is diagnosed as having and/or being a carrier for infantile myofibromatosis based on said detecting, where decreased levels of PDGFRB and/or NOTCH3 RNA and/or protein compared to normal levels of PDGFRB and/or NOTCH3 RNA and/or protein indicates the subject has or is a carrier for infantile myofibromatosis.

A further aspect of the present invention relates to a method of treating a subject having infantile myofibromatosis. This method involves selecting a subject having decreased levels of PDGFRB and/or NOTCH3 RNA and/or protein compared to a subject having normal levels of PDGFRB and/or NOTCH3 RNA and/or protein and administering a therapy suitable for treating infantile myofibromatosis to the selected subject.

Another aspect of the present invention relates to a method of preventing or treating symptoms associated with infantile myofibromatosis. This method involves selecting a subject having decreased levels of PDGFRB and/or NOTCH3 RNA and/or protein compared to a subject having normal levels of PDGFRB and/or NOTCH3 RNA and/or protein. An agent that modulates PDGFRB and/or NOTCH3 gene expression and/or PDGFRB and/or NOTCH3 encoded protein activity is administered to the selected subject under conditions effective to prevent or treat symptoms associated with infantile myofibromatosis in the subject.

A further aspect of the present invention relates to a method of treating a subject having infantile myofibromatosis. This method involves selecting a subject having a mutation in PDGFRB encoding an amino acid substitution at one or more amino acid residues corresponding to amino acid position 561 and/or 660 of SEQ ID NO:2. The method further involves administering to the selected subject an agent that reduces phosphorylation of PDGFRB under conditions effective to prevent or treat symptoms associated with infantile myofibromatosis in the subject.

As described herein in the Examples, IM gene(s) were identified using whole-exome sequencing on members of nine unrelated IM families, five who have been previously reported (see Jennings et al., "Infantile Myofibromatosis: Evidence for an Autosomal-dominant Disorder," *Am. J. Surg. Pathol.* 8:529-538 (1984); Ikediobi et al., "Infantile Myofibromatosis: Support for Autosomal Dominant Inheritance," *J. Am. Acad. Dermatol.* 49:S148-150 (2003); Zand et al., "Autosomal Dominant Inheritance of Infantile Myofibromatosis," *Am. J. Med. Genet. A.* 126:261-266 (2004); de Montpréville et al., "Endocardial Location of Familial Myofibromatosis Revealed by Cerebral Embolization: Cardiac Counterpart of the Frequent Intravascular Growth of the Disease?" *Virchows Arch.* 444:300-303 (2004)), and four new families, all whose family histories were consistent with autosomal dominant inheritance. The present invention relates to the identification of two IM genes, both involved in activating multiple cellular functions including differentiation, proliferation, and survival, both expressed in vascular smooth muscle cells and one gene product able to activate the other. Specifically, two missense mutations in the cell surface tyrosine kinase receptor PDGFRB (c.1978C>A [p.Pro660Tyr] and c.1681C>T [p.Arg561Cys]), and one missense mutation in the single pass transmembrane protein NOTCH3 (c.4556T>C, p.Leu1519Pro) were identified.

BRIEF DESCRIPTION OF THE DRAWINGS

FIG. 2A provides plots illustrating representative sequence chromatograms for each of the different mutations identified. FIG. 2B illustrates the conservation of the mutations and the surrounding region in vertebrates. Arrowheads indicate the positions of the mutated alleles.

FIG. 3 is a table showing the results of exome sequencing in which three missense mutations have been identified in two genes causing autosomal dominant IM in nine unrelated families, i.e., c.1978C>A (p.Pro660Thr) and c.1681C>T (p.Arg56lCys) in PDGFRB, and c.4556T>C (p.Leu1519Pro) in NOTCH3.

DETAILED DESCRIPTION OF THE INVENTION

Figure 1:
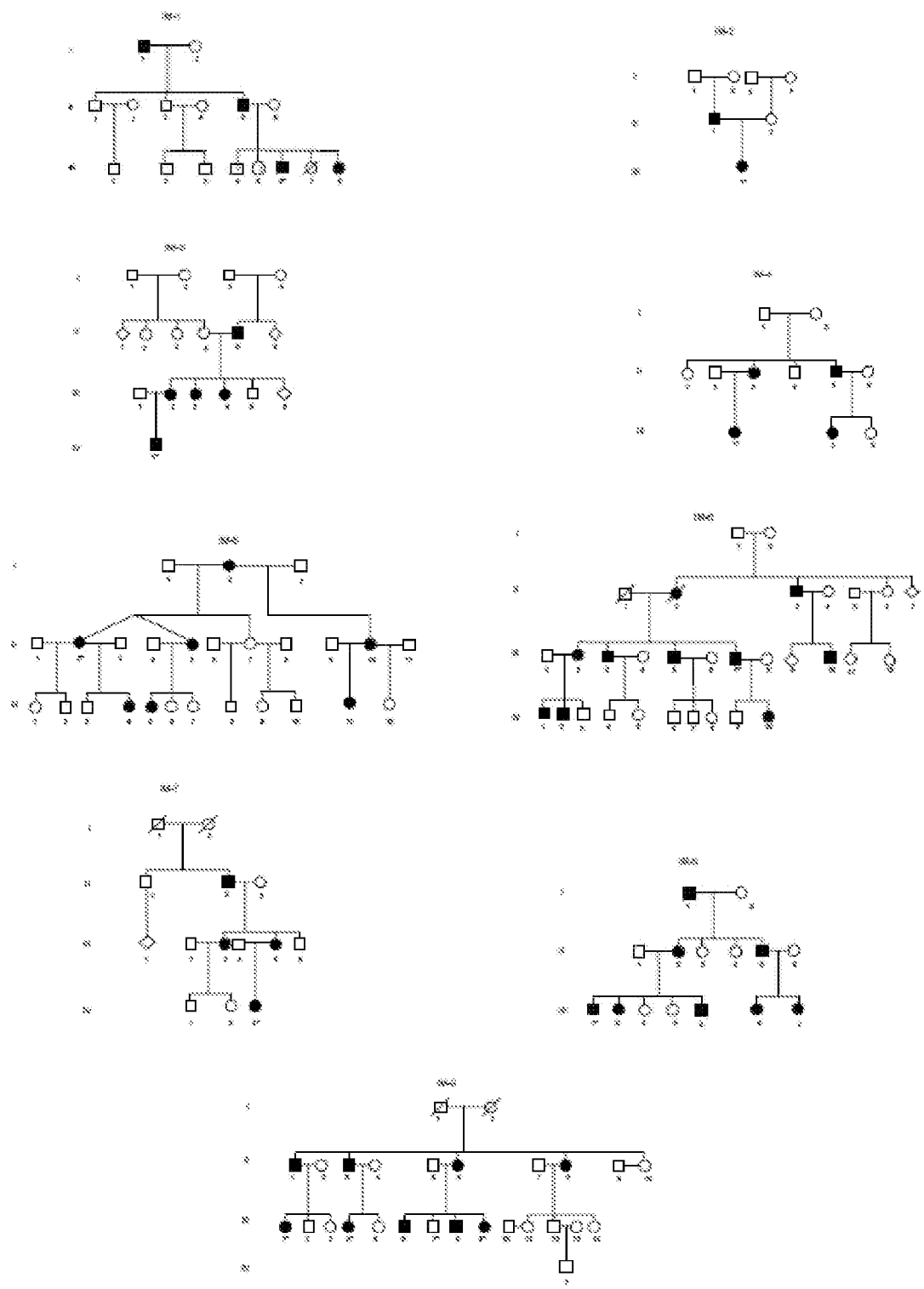
FIG. 1 illustrates the pedigrees of nine unrelated IM families. The inheritance pattern in all the families used in the Examples described herein was consistent with autosomal dominant transmission. Five families have been previously reported, i.e., IM-1 (Jennings et al., "Infantile Myofibromatosis: Evidence for an Autosomal-Dominant Disorder," *Am. J. Surg. Pathol.* 8:529-538 (1984), which is hereby incorporated by reference in its entirety), IM-2 (Ikediobi et al., "Infantile Myofibromatosis: Support for Autosomal Dominant Inheritance," *J. Am. Acad. Dermatol.* 49:S148-150 (2003), which is hereby incorporated by reference in its entirety), IM-6 (Zand et al., "Autosomal Dominant Inheritance of Infantile Myofibromatosis," *Am. J. Med. Genet. A.* 126:261-266 (2004), which is hereby incorporated by reference in its entirety), IM-7 (Zand et al., "Autosomal Dominant Inheritance of Infantile Myofibromatosis," *Am. J. Med. Genet. A.* 126:261-266 (2004), which is hereby incorporated by reference in its entirety), and IM-8 (de Montpréville et al., "Endocardial Location of Familial Myofibromatosis Revealed by Cerebral Embolization: Cardiac Counterpart of the Frequent Intravascular Growth of the Disease?" *Virchows Arch.* 444:300-303 (2004), which is hereby incorporated by reference in its entirety). *These samples were whole-exome sequenced.

The present invention relates to the identification of genes associated with an autosomal dominant inheritance pattern of infantile myofibromatosis. In a first aspect, the present invention relates to a method of diagnosing a subject as having and/or being a carrier for infantile myofibromatosis. This method involves providing an isolated biological sample from a subject; contacting the sample with one or more reagents suitable for detecting the presence or absence of one or more mutations in PDGFRB and/or NOTCH3; detecting, in the sample, the presence or absence of the one or more mutations in PDGFRB and/or NOTCH3 based on said contacting; and diagnosing the subject as having and/or being a carrier for infantile myofibromatosis based on said detecting, where the presence of the one or more mutations in PDGFRB and/or NOTCH3 indicates the subject has a mutation that causes infantile myofibromatosis.

According to the present invention, mutations in PDGFRB and NOTCH3 have been identified that predict that a subject is a carrier for or has infantile myofibromatosis. Specifically, detecting in a biological sample from a subject the presence of one or more of these mutations, predicts that the subject is a carrier for or has infantile myofibromatosis.

Thus, according to this aspect of the present invention, an isolated biological sample from a subject is provided. The biological sample may be any sample containing genetic information about the PDGFRB and/or NOTCH3 gene of the subject. In one embodiment, the sample is a blood sample from the subject.

In carrying out this method, once the isolated biological sample is isolated, the sample is contacted with one or more reagents suitable for detecting the presence or absence of one or more mutations in PDGFRB and/or NOTCH3. Suitable reagents will depend on the particular mutation being detected, and the particular method of detecting the mutation, which are now described as follows.

In one embodiment, the one or more mutations detected in a biological sample from a subject includes mutations specific to the PDGFRB gene. The mRNA and amino acid sequences for human PDGFRB are provided in GenBank Accession No. NM 002609, and as SEQ ID NO:1 and SEQ ID NO:2, respectively as set forth below.

The cDNA sequence of PDGFRB is SEQ ID NO:1, as follows:

```
ctcctgaggc tgccagcagc cagcagtgac tgcccgccct
atctgggacc caggatcgct ctgtgagcaa cttggagcca
gagaggagat caacaaggag gaggagagag ccggcccctc
agccctgctg cccagcagca gcctgtgctc gccctgccca
acgcagacag ccagacccag ggcggcccct ctggcggctc
tgctcctccc gaaggatgct tggggagtga ggcgaagctg
ggccgctcct ctcccctaca gcagcccct tcctccatcc
ctctgttctc ctgagccttc aggagcctgc accagtcctg
cctgtccttc tactcagctg ttacccactc tgggaccagc
agtctttctg ataactggga gagggcagta aggaggactt
cctggagggg gtgactgtcc agagcctgga actgtgccca
caccagaagc catcagcagc aaggacacca tgcggcttcc
gggtgcgatg ccagctctgg ccctcaaagg cgagctgctg
ttgctgtctc tcctgttact tctgaaccca cagatctctc
agggcctggt cgtcacaccc ccggggccag agcttgtcct
caatgtctcc agcaccttcg ttctgacctg ctcggttca
gctccggtgg tgtgggaacg gatgtcccag gagccccac
aggaaatggc caaggcccag gatggcacct tctccagcgt
gctcacactg accaacctca ctgggctaga cacgggagaa
tacttttgca cccacaatga ctcccgtgga ctgagaccg
atgagcggaa acggctctac atctttgtgc cagatccac
cgtgggcttc ctccctaatg atgccgagga actattcatc
tttctcacgg aaataactga gatcaccatt ccatgccgag
```

-continued

```
taacagaccc acagctggtg gtgacactgc acgagaagaa
aggggacgtt gcactgcctg tccctatga tcaccaacgt
ggcttttctg gtatctttga ggacagaagc tacatctgca
aaaccaccat tgggacagg gaggtggatt ctgatgccta
ctatgtctac agactccagg tgtcatccat caacgtctct
gtgaacgcag tgcagactgt ggtccgccag ggtgagaaca
tcaccctcat gtgcattgtg atcgggaatg aggtggtcaa
cttcgagtgg acatacccc gcaaagaaag tgggcggctg
gtggagccgg tgactgactt cctcttggat atgccttacc
acatccgctc catcctgcac atccccagtg ccgagttaga
agactcgggg acctacacct gcaatgtgac ggagagtgtg
aatgaccatc aggatgaaaa ggccatcaac atcaccgtgg
ttgagagcgg ctacgtgcgc ctcctgggag aggtgggcac
actacaatt gctgagctgc atcggagccg gacactgcag
gtagtgttcg aggcctaccc accgcccact gtcctgtggt
tcaaagacaa ccgcaccctg ggcgactcca gcgctggcga
aatcgccctg tccacgcgca acgtgtcgga gacccggtat
gtgtcagagc tgacactggt tcgcgtgaag gtggcagagg
ctggccacta ccatgcgg gccttccatg aggatgctga
ggtccagctc tccttccagc tacagatcaa tgtccctgtc
cgagtgctgg agctaagtga gagccaccct gacagtgggg
aacagacagt ccgctgtcgt ggccggggca tgccccagcc
gaacatcatc tggtctgcct gcagagacct caaaaggtgt
ccacgtgagc tgccgcccac gctgctgggg aacagttccg
aagaggagag ccagctggag actaacgtga cgtactggga
ggaggagcag gagtttgagg tggtgagcac actgcgtctg
cagcacgtgg atcggccact gtcggtgcgc tgcacgctgc
gcaacgctgt gggccaggac acgcaggagg tcatcgtggt
gccacactcc ttgcccttta aggtggtggt gatctcagcc
atcctggccc tggtggtgct caccatcatc tcccttatca
tcctcatcat gctttggcag aagaagccac gttacgagat
ccgatggaag gtgattgagt ctgtgagctc tgacggccat
gagtacatct acgtggaccc catgcagctg ccctatgact
ccacgtggga gctgccgcgg gaccagcttg tgctgggacg
caccctcggc tctgggcct ccgggcaggc ggtggaggcc
acggctcatg gcctgagcca caccctcggc tctggggcct
ttgggcaggt ggtgaggcc acggctcatg gcctgagcca
ttctcaggcc acgatgaaag tggccgtcaa gatgcttaaa
tccacagccc gcagcagtga aagcaagcc cttatgtcgg
agctgaagat catgagtcac cttgggcccc acctgaacgt
ggtcaacctg ttgggggcct gcaccaaagg aggacccatc
```

-continued

```
tatatcatca ctgagtactg ccgctacgga gacctggtgg actacctgca ccgcaacaaa cacaccttcc tgcagcacca ctccgacaag cgccgcccgc ccagcgcgga gctctacagc aatgctctgc ccgttgggct ccccctgccc agccatgtgt ccttgaccgg ggagagcgac ggtggctaca tggacatgag caaggacgag tcggtggact atgtgcccat gctggacatg aaaggagacg tcaaatatgc agacatcgag tcctccaact acatggcccc ttacgataac tacgttccct ctgccctga gaggacctgc cgagcaactt tgatcaacga gtctccagtg ctaagctaca tggacctcgt gggcttcagc taccaggtgg ccaatggcat ggagtttctg gcctccaaga actgcgtcca cagagacctg gcggctagga acgtgctcat ctgtgaaggc aagctggtca agatctgtga ctttggcctg gctcgagaca tcatgcggga ctcgaattac atctccaaag gcagcacctt tttgccttta aagtggatgg ctccggagag catcttcaac agcctctaca ccaccctgag cgacgtgtgg tccttcggga tcctgctctg ggagatcttc accttgggtg gcaccccta cccagagctg cccatgaacg agcagttcta caatgccatc aaacggggtt accgcatggc ccagcctgcc catgcctccg acgagatcta tgagatcatg cagaagtgct gggaagagaa gtttgagatt cggccccct tctcccagct ggtgctgctt ctcgagagac tgttgggcga aggttacaaa aagaagtacc agcaggtgga tgaggagttt ctgaggagtg accacccagc catccttcgg tcccaggccc gcttgcctgg gttccatggc ctccgatctc ccctggacac cagctccgtc ctctatactg ccgtgcagcc caatgagggt gacaacgact atatcatccc cctgcctgac cccaaacccg aggttgctga cgagggccca ctggagggtt ccccccagcct agccagctcc accctgaatg aagtcaacac ctcctcaacc atctcctgtg acagccccct ggagccccag gacgaaccag agccagagcc ccagcttgag ctccaggtgg agccggagcc agagctggaa cagttgccgg attcggggtg ccctgcgcct cgggcggaag cagaggatag cttcctgtag ggggctggcc cctaccctgc cctgcctgaa gctcccccc tgccagcacc cagcatctcc tggcctggcc tgaccgggct tcctgtcagc caggctgccc ttatcagctg tccccttctg gaagctttct gctcctgacg tgttgtgccc caaaccctgg ggctggctta ggaggcaaga aaactgcagg ggccgtgacc agccctctgc ctccaggag gccaactgac tctgagccag ggttccccca gggaactcag ttttcccata tgtaagatgg gaaagttagg cttgatgacc cagaatctag gattctctcc ctggctgaca ggtggggaga ccgaatccct
```

-continued

```
ccctgggaag attcttggag ttactgaggt ggtaaattaa cttttttctg ttcagccagc tacccctcaa ggaatcatag ctctctcctc gcactttat ccacccagga gctagggaag agaccctagc ctccctggct gctggctgag ctagggccta gccttgagca gtgttgcctc atccagaaga aagccagtct cctccctatg atgccagtcc ctgcgttccc tggcccgagc tggtctgggg ccattaggca gcctaattaa tgctggaggc tgagccaagt acaggacacc cccagcctgc agcccttgcc cagggcactt ggagcacacg cagccatagc aagtgcctgt gtccctgtcc ttcaggccca tcagtcctgg gcttttttct ttatcaccct cagtcttaat ccatccacca gagtctagaa ggccagacgg gccccgcatc tgtgatgaga atgtaaatgt gccagtgtgg agtgccacg tgtgtgtgcc agtatatggc cctggctctg cattggacct gctatgaggc tttggaggaa tccctcaccc tctctgggcc tcagtttccc cttcaaaaaa tgaataagtc ggacttatta actctgagtg ccttgccagc actaacattc tagagtattc caggtggttg cacatttgtc cagatgaagc aaggccatat accctaaact tccatcctgg gggtcagctg ggctcctggg agattccaga tcacacatca cactctgggg actcaggaac catgccccctt ccccaggccc ccagcaagtc tcaagaacac agctgcacag gccttgactt agagtgacag ccggtgtcct ggaaagcccc cagcagctgc cccagggaca tgggaagacc acgggacctc tttcactacc cacgatgacc tccgggggta tcctgggcaa aagggacaaa gagggcaaat gagatcacct cctgcagccc accactccag cacctgtgcc gaggtctgcg tcgaagacag aatggacagt gaggacagtt atgtcttgta aaagacaaga agcttcagat gggtacccca agaaggatgt gagaggtggg cgctttggag gtttgcccct cacccaccag ctgccccatc cctgaggcag cgctccatgg gggtatggtt ttgtcactgc ccagacctag cagtgacatc tcattgtccc cagcccagtg ggcattggag gtgccagggg agtcagggtt gtagccaaga cgccccgca cggggagggt tgggaagggg gtgcaggaag ctcaaccct ctgggcacca accctgcatt gcaggttggc accttacttc cctgggatcc ccagagttgg tccaaggagg gagagtgggt tctcaatacg gtaccaaaga tataatcacc taggtttaca aatatttta ggactcacgt taactcacat ttatacagca gaaatgctat tttgtatgct gttaagtttt tctatctgtg tacttttttt taagggaaag atttaatat taaacctggt gcttctcact cacaaaaaa
```

The amino acid sequence encoded by PDGFRB is SEQ ID NO:2, as follows:

```
MRLPGAMPAL ALKGELLLLS LLLLLEPQIS QGLVVTPPGP
ELVLNVSSTF VLTCSGSAPV VWERMSQEPP QEMAKAQDGT
FSSVLTLTNL TGLDTGEYFC THNDSRGLET DERKRLYIFV
PDPTVGFLPN DAEELFIFLT EITEITIPCR VTDPQLVVTL
HEKKGDVALP VPYDHQRGFS GIFEDRSYIC KTTIGDREVD
SDAYYVYRLQ VSSINVSVNA VQTVVRQGEN ITLMCIVIGN
EVVNFEWTYP RKESGRLVEP VTDFLLDMPY HIRSILHIPS
AELEDSGTYT CNVTESVNDH QDEKAINITV VESGYVRLLG
EVGTLQFAEL HRSRTLQVVF EAYPPPTVLW FKDNRTLGDS
SAGEIALSTR NVSETRYVSE LTLVRVKVAE AGHYTMRAFH
EDAEVQLSFQ LQINVPVRVL ELSESHPDSG EQTVRCRGRG
MPQPNIIWSA CRDLKRCPRE LPPTLLGNSS EEESQLETNV
TYWEEEQEFE VVSTLRLQHV DRPLSVRCTL RNAVGQDTQE
VIVVPHSLPF KVVVISAILA LVVLTIISLI ILIMLWQKKP
RYEIRWKVIE SVSSDGHEYI YVDPMQLPYD STWELPRDQL
VLGRTLGSGA FGQVVEATAH GLSHSQATMK VAVKMLKSTA
RSSEKQALMS ELKIMSHLGP HLNVVNLLGA CTKGGPIYII
TEYCRYGDLV DYLHRNKHTF LQHHSDKRRP PSAELYSNAL
PVGLPLPSHV SLTGESDGGY MDMSKDESVD YVPMLDMKGD
VKYADIESSN YMAPYDNYVP SAPERTCRAT LINESPVLSY
MDLVGFSYQV ANGMEFLASK NCVHRDLAAR NVLICEGKLV
KICDFGLARD IMRDSNYISK GSTFLPLKWM APESIFNSLY
TTLSDVWSFG ILLWEIFTLG GTPYPELPMN EQFYNAIKRG
YRMAQPAHAS DEIYEIMQKC WEEKFEIRPP FSQLVLLLER
LLGEGYKKKY QQVDEEFLRS DHPAILRSQA RLPGFHGLRS
PLDTSSVLYT AVQPNEGDND YIIPLPDPKP EVADEGPLEG
SPSLASSTLN EVNTSSTISC DSPLEPQDEP EPEPQLELQV
EPEPELEQLP DSGCPAPRAE AEDSFL
```

Specific mutations in PDGFRB which are indicative of having IM and/or being an autosomal dominant carrier of IM include amino acid substitutions at one or more amino acid residues corresponding to amino acid positions 561 and/or 660 of SEQ ID NO:2.

According to one embodiment, the amino acid substitution comprises an arginine to cysteine substitution at the amino acid position corresponding to Arg561 of SEQ ID NO:2.

According to another embodiment, the amino acid substitution comprises a proline to threonine substitution at the amino acid position corresponding to Pro660 of SEQ ID NO:2.

In one embodiment, the one or more mutations detected in a biological sample from a subject includes one or more mutations specific to the NOTCH3 gene. The mRNA and amino acid sequences for human NOTCH3 are provided in GenBank Accession No. NM_000435, and as SEQ ID NO:3 and SEQ ID NO:4, respectively as set forth below.

The cDNA sequence of NOTCH3 is SEQ ID NO:3, as follows:

```
gcggcgcgga ggctggcccg ggacgcgccc ggagcccagg
gaaggaggga ggaggggagg gtcgcggccg gccgccatgg
ggccggggc ccgtggccgc cgccgccgcc gtcgcccgat
gtcgccgcca ccgccaccgc cacccgtgcg ggcgctgccc
ctgctgctgc tgctagcggg gccggggct gcagcccccc
cttgcctgga cggaagcccg tgtgcaaatg gaggtcgttg
cacccagctg ccctcccggg aggctgcctg cctgtgcccg
cctggctggg tgggtgagcg gtgtcagctg gaggacccct
gtcactcagg ccctgtgct ggccgtggtg tctgccagag
ttcagtggtg gctggcaccg cccgattctc atgccggtgc
ccccgtggct tccgaggccc tgactgctcc ctgccagatc
cctgcctcag cagcccttgt gcccacgtgt cccgctgctc
agtggggccc gatggacgct tcctctgctc ctgcccacct
ggctaccagg gccgcagctg ccgaagcgac gtggatgagt
gccgggtggg tgagccctgc cgccatggtg gcacctgcct
caacacacct ggctccttcc gctgccagtg tccagctggc
tacacagggc cactatgtga aacccccgcg gtgccctgtg
caccctcacc atgccgtaac gggggcacct gcaggcagag
tggcgacctc acttacgact gtgcctgtct tcctgggttt
gagggtcaga attgtgaagt gaacgtggac gactgtccag
gacaccgatg tctcaatggg ggacatgcg tggatggcgt
caacaccat aactgccagt gccctcctga gtggacaggc
cagttctgca cggaggacgt ggatgagtgt cagctgcagc
ccaacgcctg ccacaatggg ggtacctgct tcaacacgct
gggtggccac agctgcgtgt gtgtcaatgg ctggacaggc
gagagctgca gtcagaatat cgatgactgt gccacagccg
tgtgcttcca tggggccacc tgccatgacc gcgtggcttc
tttctactgt gcctgcccca tgggcaagac tggcctcctg
tgtcacctgg atgacgcctg tgtcagcaac ccctgccacg
aggatgctat ctgtgacaca aatccggtga acggccggc
catttgcacc tgtcctcccg gcttcacggg tggggcatgt
gaccaggatg tggacgagtg ctatcggc gccaaccct
gcgagcactt gggcaggtgc gtgaacacgc agggctcctt
cctgtgccag tgcggtcgtg gctacactgg acctcgctgt
gagaccgatg tcaacgagtg tctgtcgggg ccctgccgaa
accaggccac gtgcctcgac cgcataggcc agttcacctg
tatctgtatg gcaggcttca caggaaccta ttgcgaggtg
gacattgacg agtgtcagag tagcccctgt gtcaacggtg
gggtctgcaa ggaccgagtc aatggcttca gctgcacctg
```

-continued

```
cccctcgggc ttcagcggct ccacgtgtca gctggacgtg
gacgaatgcg ccagcacgcc ctgcaggaat ggcgccaaat
gcgtggacca gcccgatggc tacgagtgcc gctgtgccga
gggctttgag gcacgctgt gtgatcgcaa cgtggacgac
tgctcccctg acccatgcca ccatggtcgc tgcgtggatg
gcatcgccag cttctcatgt gcctgtgctc ctggctacac
gggcacacgc tgcgagagcc aggtggacga atgccgcagc
cagccctgcc gccatggcgg caaatgccta gacctggtgg
acaagtacct ctgccgctgc ccttctggga ccacaggtgt
gaactgcgaa gtgaacattg acgactgtgc cagcaacccc
tgcacctttg agtctgccg tgatggcatc aaccgctacg
actgtgtctg ccaacctggc ttcacagggc cccttgtaa
cgtggagatc aatgagtgtg cttccagccc atgcggcgag
ggaggttcct gtgtggatgg ggaaaatggc ttccgctgcc
tctgccgcc tggctccttg cccccactct gcctccccc
gagccatccc tgtgcccatg agccctgcag tcacggcatc
tgctatgatg cacctggcgg gttccgctgt gtgtgtgagc
ctggctggag tggcccccgc tgcagccaga gcctggcccg
agacgcctgt gagtcccagc cgtgcagggc cggtgggaca
tgcagcagcg atggaatggg tttccactgc acctgccgc
ctggtgtcca gggacgtcag tgtgaactcc tctccccctg
caccccgaac ccctgtgagc atgggggccg ctgcgagtct
gcccctggcc agctgccgt ctgctcctgc ccccagggct
ggcaaggccc acgatgccag caggatgtgg acgagtgtgc
tggccccgca ccctgtggcc tcatggtat ctgcaccaac
ctggcaggga gtttcagctg cacctgccat ggagggtaca
ctggcccttc ctgcgatcag gacatcaatg actgtgaccc
caacccatgc ctgaacggtg gctcgtgcca agacggcgtg
ggctccttt cctgctcctg cctccctggt ttcgccggcc
cacgatgcgc ccgcgatgtg gatgagtgcc tgagcaaccc
ctgcggcccg ggcacctgta ccgaccacgt ggcctccttc
acctgcacct gcccgccagg ctacggaggc ttccactgcg
aacaggacct gcccgactgc agccccagct cctgcttcaa
tggcgggacc tgtgtggacg gcgtgaactc gttcagctgc
ctgtgccgtc ccggctacac aggagcccac tgccaacatg
aggcagaccc ctgcctctcg cggccctgcc tacacggggg
cgtctgcagc gccgccacc tggcttccg ctgcacctgc
ctcgagagct tcacgggccc gcagtgccag acgctggtgg
attggtgcag ccgccagcct tgtcaaaacg ggggtcgctg
cgtccagact ggggcctatt gccttgtcc ccctggatgg
agcggacgcc tctgtgacat ccgaagcttg ccctgcaggg
```

-continued

```
aggccgcagc ccagatcggg gtgcggctgg agcagctgtg
tcaggcgggt gggcagtgtg tggatgaaga cagctcccac
tactgcgtgt gcccagaggg ccgtactggt agccactgtg
agcaggaggt ggaccctgc ttggcccagc cctgccagca
tgggggacc tgccgtggct atatggggg ctacatgtgt
gagtgtcttc ctggctacaa tggtgataac tgtgaggacg
acgtggacga gtgtgcctcc cagccctgcc agcacggggg
ttcatgcatt gacctcgtgg cccgctatct ctgctcctgt
ccccaggaa cgctgggggt gctctgcgag attaatgagg
atgactgcgg cccaggccca ccgctggact cagggccccg
gtgcctacac aatggcacct gcgtggacct ggtgggtggt
ttccgctgca cctgtccccc aggatacact ggtttgcgct
gcgaggcaga catcaatgag tgtcgctcag gtgcctgcca
cgcggcacac acccgggact gcctgcagga cccaggcgga
ggtttccgtt gccttttgtca tgctggcttc tcaggtcctc
gctgtcagac tgtcctgtct ccctgcgagt cccagccatg
ccagcatgga ggccagtgcc gtcctagccc gggtcctggg
ggtgggctga ccttcacctg tcactgtgcc cagccgttct
ggggtccgcg ttgcgagcgt gtgcgcgct cctgccggga
gctgcagtgc ccggtgggcg tcccatgcca gcagacgccc
cgcgggccgc gctgcgcctc cccccaggg ttgtcgggac
cctcctgccg cagcttcccg gggtcgccgc cggggccag
caacgccagc tgcgcggcc cccctgtct ccacgggggc
tcctgccgcc ccgcgccgct cgcgcccttc ttccgctgcg
cttgcgcgca gggctggacc gggccgcgct gcgaggcgcc
cgccgcggca cccgaggtct cggaggagcc gcggtgcccg
cgcgccgcct gccaggccaa gcgcggggac cagcgctgcg
accgcgagtg caacagccca ggctgcggct gggacggcgg
cgactgctcg ctgagcgtgg gcgaccctg gcggcaatgc
gaggcgctgc agtgctggcg cctcttcaac aacagccgct
gcgacccgc ctgcagctcg cccgcctgcc tctacgacaa
cttcgactgc cacgccggtg gccgcgagcg cacttgcaac
ccggtgtacg agaagtactg cgccgaccac tttgccgacg
gccgctgcga ccagggctgc aacacggagg agtgcggctg
ggacgggctg gattgugcca gcgaggtgcc ggccctgctg
gcccgcggcg tgctggtgcc cacagtgctg ctgccgccag
aggagctact gcgttccagc gccgactttc tgcagcggct
cagcgccatc ctgcgcacct gctgcgctt ccgcctggac
gcgcacgcc aggccatggt cttcccttac caccggccta
gtcctggctc cgaacccggg gcccgtcggg agctggcccc
cgaggtgatc ggctcggtag taatgctgga gattgacaac
```

-continued cggctctgcc tgcagtcgcc tgagaatgat cactgcttcc
ccgatgccca gagcgccgct gactacctgg gagcgttgtc
agcggtggag cgcctggact tcccgtaccc actgcgggac
gtgcgggggg agccgctgga gcctccagaa cccagcgtcc
cgctgctgcc actgctagtg gcgggcgctg tcttgctgct
ggtcattctc gtcctgggtg tcatggtggc ccggcgcaag
cgcgagcaca gcaccctctg gttccctgag ggcttctcac
tgcacaagga cgtggcctct ggtcacaagg gccggcggga
acccgtgggc caggacgcgc tgggcatgaa gaacatggcc
aagggtgaga gcctgatggg ggaggtggcc acagactgga
tggacacaga gtgcccagag gccaagcggc taaaggtaga
ggagccaggc atgggggctg aggaggctgt ggattgccgt
cagtggactc aacaccatct ggttgctgct gacatccgcg
tggcaccagc catggcactg acaccaccac agggcgacgc
agatgctgat ggcatggatg tcaatgtgcg tggcccagat
ggcttcaccc cgctaatgct ggcttccttc tgtgggggg
ctctggagcc aatgccaact gaagaggatg aggcagatga
cacatcagct agcatcatct ccgacctgat ctgccagggg
gctcagcttg gggcacggac tgaccgtact ggcgagactg
ctttgcacct ggctgcccgt tatgcccgtg ctgatgcagc
caagcggctg ctggatgctg gggcagacac caatgcccag
gaccactcag gccgcactcc cctgcacaca gctgtcacag
ccgatgccca gggtgtcttc cagattctca tccgaaaccg
ctctacagac ttggatgccc gcatggcaga tggctcaacg
gcactgatcc tggcggcccg cctggcagta gagggcatgg
tggaagagct catcgccagc catgctgatg tcaatgctgt
ggatgagctt gggaaatcag ccttacactg gctgcggct
gtgaacaacg tggaagccac tttggccctg ctcaaaaatg
gagccaataa ggacatgcag gatagcaagg aggagacccc
cctattcctg gccgcccgcg agggcagcta tgaggctgcc
aagctgctgt tggaccactt tgccaaccgt gagatcaccg
accacctgga caggctgccg cgggacgtag cccaggagag
actgcaccag acatcgtgc gcttgctgga tcaacccagt
gggccccgca gccccccgg tccccacggc ctggggcctc
tgctctgtcc tccaggggcc ttcctccctg gcctcaaagc
ggcacagtcg gggtccaaga agagcaggag gccccccggg
aaggcgggc tggggccgca ggggccccgg gggcggggca
agaagctgac gctggcctgc ccggccccc tggctgacag
ctcggtcacg ctgtcgcccg tggactcgct ggactcccg
cggcctttcg gtgggccccc tgcttccccct ggtggcttcc
cccttgaggg gccctatgca gctgccactg ccactgcagt -continued gtctctggca cagcttggtg gcccaggccg gcgggtcta
gggcgccagc cccctggagg atgtgtactc agcctgggcc
tgctgaaccc tgtggctgtg ccctcgatt gggcccggct
gccccacct gcccctccag gccctcgtt cctgctgcca
ctggcgccgg gaccccagct gctcaaccca gggaccccg
tctccccgca ggagcggccc ccgccttacc tggcagtccc
aggacatggc gaggagtacc cggcggctgg ggcacacagc
agcccccaa aggcccgctt cctgcgggtt cccagtgagc
acccttacct gaccccatcc cccgaatccc ctgagcactg
ggccagcccc tcacctccct ccctctcaga ctggtccgaa
tccacgccta gcccagccac tgccactggg gccatggcca
ccaccactgg ggcactgcct gcccagccac ttcccttgtc
tgttcccagc tcccttgctc aggcccagac ccagctgggg
ccccagccgg aagttacccc caagaggcaa gtgttggcct
gagacgctcg tcagttctta gatcttgggg gcctaaagag
accccgtcc tgcctccttt ctttctctgt ctcttccttc
cttttagtct ttttcatcct cttctctttc caccaaccct
cctgcatcct tgccttgcag cgtgaccgag ataggtcatc
agcccaggc ttcagtcttc ctttatttat aatgggtggg
ggctaccacc caccctctca gtcttgtgaa gagtctggga
cctccttctt ccccacttct ctcttccctc attcctttct
ctctccttct ggcctctcat ttccttacac tctgacatga
atgaattatt attatttta tttttcttt tttttttaca
ttttgtatag aaacaaattc atttaaacaa acttattatt
attattttt acaaaatata tatatggaga tgctccctcc
ccctgtgaac cccccagtgc cccgtggg ctgagtctgt
gggcccattc ggccaagctg gattctgtgt acctagtaca
caggcatgac tgggatcccg tgtaccgagt acacgaccca
ggtatgtacc aagtaggcac ccttgggcgc acccactggg
gccaggggtc gggggagtgt tgggagcctc ctccccaccc
cacctccctc acttcactgc attccagatg ggacatgttc
catagccttg ctggggaagg gcccactgcc aactccctct
gccccagccc cacccttggc catctccctt tgggaactag
ggggctgctg gtgggaaatg ggagccaggg cagatgtatg
cattcctttg tgtccctgta aatgtgggac tacaagaaga
ggagctgcct gagtggtact ttctcttcct ggtaatcctc
tggcccagcc tcatggcaga atagaggtat ttttaggcta
tttttgtaat atggcttctg gtcaaaatcc ctgtgtagct
gaattcccaa gccctgcatt gtacagcccc ccactcccct
caccacctaa taaaggaata gttaacactc aaaaaaaaaa
aaaaaaaa The amino acid sequence encoded by NOTCH3 is SEQ ID NO:4, as follows:

```
MGPGARGRRR RRRPMSPPPP PPPVRALPLL LLLAGPGAAA
PPCLDGSPCA NGGRCTQLPS REAACLCPPG WVGERCQLED
PCHSGPCAGR GVCQSSVVAG TARFSCRCPR GFRGPDCSLP
DPCLSSPCAH GARCSVGPDG RFLCSCPPGY QGRSCRSDVD
ECRVGEPCRH GGTCLNTPGS FRCQCPAGYT GPLCENPAVP
CAPSPCRNGG TCRQSGDLTY DCACLPGFEG QNCEVNVDDC
PGHRCLNGGT CVDGVNTYNC QCPPEWTGQF CTEDVDECQL
QPNACHNGGT CFNTLGGHSC VCVNGWTGES CSQNIDDCAT
AVCFHGATCH DRVASFYCAC PMGKTGLLCH LDDACVSNPC
HEDAICDTNP VNGRAICTCP PGFTGGACDQ DVDECSIGAN
PCEHLGRCVN TQGSFLCQCG RGYTGPRCET DVNECLSGPC
RNQATCLDRI GQFTCICMAG FTGTYCEVDI DECQSSPCVN
GGVCKDRVNG FSCTCPSGFS GSTCQLDVDE CASTPCRNGA
KCVDQPDGYE CRCAEGFEGT LCDRNVDDCS PDPCHHGRCV
DGIASFSCAC APGYTGTRCE SQVDECRSQP CRHGGKCLDL
VDKYLCRCPS GTTGVNCEVN IDDCASNPCT FGVCRDGINR
YDCVCQPGFT GPLCNVEINE CASSPCGEGG SCVDGENGFR
CLCPPGSLPP LCLPPSHPCA HEPCSHGICY DAPGGFRCVC
EPGWSGPRCS QSLARDACES QPCRAGGTCS SDGMGFHCTC
PPGVQGRQCE LLSPCTPNPC EHGGRCESAP GQLPVCSCPQ
GWQGPRCQQD VDECAGPAPC GPHGICTNLA GSFSCTCHGG
YTGPSCDQDI NDCDPNPCLN GGSCQDGVGS FSCSCLPGFA
GPRCARDVDE CLSNPCGPGT CTDHVASFTC TCPPGYGGFH
CEQDLPDCSP SSCFNGGTCV DGVNSFSCLC RPGYTGAHCQ
HEADPCLSRP CLHGGVCSAA HPGFRCTCLE SFTGPQCQTL
VDWCSRQPCQ NGGRCVQTGA YCLCPPGWSG RLCDIRSLPC
REAAAQIGVR LEQLCQAGGQ CVDEDSSHYC VCPEGRTGSH
CEQEVDPCLA QPCQHGGTCR GYMGGYMCEC LPGYNGDNCE
DDVDECASQP CQHGGSCIDL VARYLCSCPP GTLGVLCEIN
EDDCGPGPPL DSGPRCLHNG TCVDLVGGFR CTCPPGYTGL
RCEADINECR SGACHAAHTR DCLQDPGGGF RCLCHAGFSG
PRCQTVLSPC ESQPCQHGGQ CRPSPGPGGG LTFTCHCAQP
FWGPRCERVA RSCRELQCPV GVPCQQTPRG PRCACPPGLS
GPSCRSFPGS PPGASNASCA AAPCLHGGSC RPAPLAPFFR
CACAQGWTGP RCEAPAAAPE VSEEPRCPRA ACQAKRGDQR
CDRECNSPGC GWDGGDCSLS VGDPWRQCEA LQCWRLFNNS
RCDPACSSPA CLYDNFDCHA GGRERTCNPV YEKYCADHFA
DGRCDQGCNT EECGWDGLDC ASEVPALLAR GVLVLTVLLP
PEELLRSSAD FLQRLSAILR TSLRFRLDAH GQAMVFPYHR
PSPGSEPRAR RELAPEVIGS VVMLEIDNRL CLQSPENDHC
FPDAQSAADY LGALSAVERL DFPYPLRDVR GEPLEPPEPS
VPLLPLLVAG AVLLLVILVL GVMVARRKRE HSTLWFPEGF
SLHKDVASGH KGRREPVGQD ALGMKNMAKG ESLMGEVATD
WMDTECPEAK RLKVEEPGMG AEEAVDCRQW TQHHLVAADI
RVAPAMALTP PQGDADADGM DVNVRGPDGF TPLMLASFCG
GALEPMPTEE DEADDTSASI ISDLICQGAQ LGARTDRTGE
TALHLAARYA RADAAKRLLD AGADTNAQDH SGRTPLHTAV
TADAQGVFQI LIRNRSTDLD ARMADGSTAL ILAARLAVEG
MVEELIASHA DVNAVDELGK SALHWAAAVN NVEATLALLK
NGANKDMQDS KEETPLFLAA REGSYEAAKL LLDHFANREI
TDHLDRLPRD VAQERLHQDI VRLLDQPSGP RSPPGPHGLG
PLLCPPGAFL PGLKAAQSGS KKSRRPPGKA GLGPQGPRGR
GKKLTLACPG PLADSSVTLS PVDSLDSPRP FGGPPASPGG
FPLEGPYAAA TATAVSLAQL GGPGRAGLGR QPPGGCVLSL
GLLNPVAVPL DWARLPPPAP PGPSFLLPLA PGPQLLNPGT
PVSPQERPPP YLAVPGHGEE YPAAGAHSSP PKARFLRVPS
EHPYLTPSPE SPEHWASPSP PSLSDWSEST PSPATATGAM
ATTTGALPAQ PLPLSVPSSL AQAQTQLGPQ PEVTPKRQVL A
```

Specific mutations in NOTCH3 which are indicative of having IM and/or being an autosomal dominant carrier of IM include an amino acid substitution at an amino acid residue corresponding to amino acid position 1519 of SEQ ID NO:4.

According to one embodiment, the amino acid substitution comprises a leucine to proline substitution at the amino acid position corresponding to Leu1519 of SEQ ID NO:4.

Detecting, in a sample, the presence or absence of one or more mutations in PDGFRB and/or NOTCH3 according to the methods of the present invention is carried out using various methods. In one embodiment, detecting involves sequencing at least a portion of a nucleic acid sequence in the sample corresponding to PDGFRB and/or NOTCH3 (i.e., SEQ ID NO:1 and SEQ ID NO:3, respectively). For example, detecting can be carried out by direct sequencing of the PDGFRB and/or NOTCH3 genes, or regions of PDGFRB and/or NOTCH3 comprising the one or more mutations identified herein.

Direct sequencing assays typically involve isolating DNA sample from a subject using any suitable method known in the art, and cloning the region of interest to be sequenced into a suitable vector for amplification by growth in a host cell (e.g., bacteria) or direct amplification by PCR or other amplification assay. Following amplification, the DNA can be sequenced using any suitable method. One suitable method involves high-throughput next generation sequencing ("NGS") to identify genetic variation. Various NGS sequencing chemistries are available and suitable for use in carrying out the methods of the present invention, including pyrosequencing (Roche® 454), sequencing by reversible dye terminators (Illumina® HiSeq, Genome Analyzer and MiSeq systems), sequencing by sequential ligation of oligonucleotide probes (Life Technologies® SOLiD), and hydrogen ion semiconductor sequencing (Life Technologies®, Ion Torrent™). Alternatively, classic sequencing methods, such as the Sanger chain termination method or Maxam-Gilbert sequencing can be used to carry out the methods of the present invention.

In another embodiment, detecting, in a sample, the presence or absence of one or more mutations in PDGFRB and/or NOTCH3 according to the methods of the present invention is carried out with a hybridization assay. This involves using one or more oligonucleotide probes having a nucleotide sequence that is complementary to a nucleotide sequence of a nucleic acid molecule in a sample comprising the one or more mutations in PDGFRB and/or NOTCH3. The oligonucleotide probes are designed to be complementary to the wildtype, non-mutant nucleotide sequence and/or the mutant nucleotide sequence of PDGFRB and/or NOTCH3 to effectuate the detection of the presence or the absence of the mutation in the sample from the subject upon contacting the sample with the oligonucleotide probes. A variety of hybridization assays that are known in the art are suitable for use in this embodiment. For example, and without limitation, the following methods may be used: direct hybridization assays, such as northern blot or Southern blot (see e.g., Ausabel et al., Current Protocols in Molecular Biology, John Wiley & Sons, NY (1991), which is hereby incorporated by reference in its entirety). Alternatively, direct hybridization can be carried out using an array based method where a series of oligonucleotide probes designed to be complementary to a particular non-mutant or mutant gene region are affixed to a solid support. The DNA sample from the subject is contacted with the array containing the oligonucleotide probes, and hybridization of nucleic acid molecules from the sample to their complementary oligonucleotide probes on the array surface is detected. Examples of direct hybridization array platforms include, without limitation, the Affymetrix GeneChip or SNP arrays and Illumina's Bead Array.

Other common genotyping methods include, but are not limited to, restriction fragment length polymorphism assays; amplification based assays, such as molecular beacon assays; nucleic acid arrays; allele-specific PCR; primer extension assays, such as allele-specific primer extension (e.g., Illumina® Infinium® assay), arrayed primer extension (see Krjutskov et al., "Development of a Single Tube 640-ples Genotyping Method for Detection of Nucleic Acid Variations on Microarrays," *Nucleic Acids Res.* 36(12) e75 (2008), which is hereby incorporated by reference in its entirety); homogeneous primer extension assays; primer extension with detection by mass spectrometry (e.g., Sequenom® iPLEX SNP genotyping assay) (see Zheng et al., "Cumulative Association of Five Genetic Variants with Prostate Cancer," *N. Eng. J. Med.* 358(9):910-919 (2008), which is hereby incorporated by reference in its entirety); multiplex primer extension sorted on genetic arrays; flap endonuclease assays (e.g., the Invader® assay) (see Olivier M., "The Invader Assay for SNP Genotyping," *Mutat. Res.* 573:103-110 (2005), which is hereby incorporated by reference in its entirety); 5' nuclease assays, such as the TaqMan® assay (see U.S. Pat. No. 5,210,015 to Gelfand et al. and U.S. Pat. No. 5,538,848 to Livak et al., both of which are hereby incorporated by reference in their entirety); oligonucleotide ligation assays, such as ligation with rolling circle amplification, homogeneous ligation, OLA (see U.S. Pat. No. 4,988,617 to Landgren et al., which is hereby incorporated by reference in its entirety), and multiplex ligation reactions followed by PCR where zipcodes are incorporated into ligation reaction probes and amplified PCR products are determined by electrophoretic or universal zipcode array readout (see U.S. Pat. Nos. 7,429,453 and 7,312,039 to Barany et al., both of which are hereby incorporated by reference in their entirety). Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

Detecting, in the sample, the presence or absence of the one or more mutations in PDGFRB and/or NOTCH3 indicates the subject has a mutation that causes infantile myofibromatosis. Accordingly, the subject is diagnosed as having and/or being a carrier for infantile myofibromatosis based on said detecting in the sample.

In carrying out the methods of the present invention, a "subject" includes any animal including, without limitation, mammalian subjects such as humans, non-human primates, dogs, cats, rodents, horses, cattle, sheep, and pigs. In one embodiment, the subject is a human subject.

In one embodiment, the diagnostic method of the present invention is carried out for prenatal or neonatal testing, or to test embryos as carriers of infantile myofibromatosis.

A subject diagnosed as having infantile myofibromatosis pursuant to the method of the present invention may be administered a therapy suitable for treatment of infantile myofibromatosis. Suitable therapies may include, for example and without limitation, removal of a tumor, administering radiation therapy, administering chemotherapy, and/or modulating PDGFRB and/or NOTCH3 gene expression and/or PDGFRB and/or NOTCH3 encoded protein activity.

Another aspect of the present invention relates to a method of treating a subject having infantile myofibromatosis. This method involves selecting a subject having one or more mutations in PDGFRB and/or NOTCH3 and administering a therapy suitable for treating infantile myofibromatosis to the selected subject.

Particular mutations in PDGFRB and/or NOTCH3 and methods of detecting these mutations are described supra.

In one embodiment, the subject is undergoing treatment for infantile myofibromatosis at the time the one or more mutations in PDGFRB and/or NOTCH3 is detected. Following detection of the one or more mutations, the subject's therapy is modified to implement a more precise treatment that is suitable for treating infantile myofibromatosis. In another embodiment, the subject is not undergoing treatment for infantile myofibromatosis at the time the one or more mutations is detected, i.e., the gene mutation(s) are detected at the time of diagnosis. In accordance with this embodiment, a preferable course of treatment is determined based on the diagnosis.

As discussed supra, suitable therapies that may be administered according to this aspect of the present invention include, for example and without limitation, removal of a tumor, administering radiation therapy, administering chemotherapy, and/or modulating PDGFRB and/or NOTCH3 gene expression and/or PDGFRB and/or NOTCH3 encoded protein activity.

A further aspect of the present invention relates to a method of preventing or treating symptoms associated with infantile myofibromatosis. This method involves selecting a subject having one or more mutations in PDGFRB and/or NOTCH3 and administering to the selected subject an agent that modulates PDGFRB and/or NOTCH3 gene expression and/or PDGFRB and/or NOTCH3 encoded protein activity under conditions effective to prevent or treat symptoms associated with infantile myofibromatosis in the subject.

In one embodiment, the selected subject is administered an agent that modulates PDGFRB gene expression and/or PDGFRB encoded protein activity. Agents that are known to modulate PDGFRB gene expression and/or PDGFRB encoded protein activity include, without limitation, GLEEVEC® (imatinib mesylate) (see Gibbs et al., "Decoupling of Tumor-initiating Activity from Stable Immunophenotype in HoxA9-Meisl-driven AML," *Cell Stem Cell.* 10:210-217 (2012); Huang et al., "Glucosylceramide Synthase Inhibitor PDMP Sensitizes Chronic Myeloid Leukemia T315I Mutant to Bcr-AbI Inhibitor and Cooperatively Induces Glycogen Synthase Kinase-3-regulated Apoptosis," *FASEB J.* 25:3661-3673 (2011); and Yamakawa et al., "Pharmacokinetic Impact of SLCO1A2 Polymorphisms on Imatinib Disposition in Patients with Chronic Myeloid Leukemia," *Clin. Pharmacol. Ther.* 90:157-163 (2011), which are hereby incorporated by reference in its entirety); imatinib mesylate (see Griaud et al., "A Pathway from leukemogenic Oncogenes and Stem Cell Chemokines to RNA Processing via TH005," *Leukemia* 27:932-940 (2013); Huang et al., "Glucosylceramide Synthase Inhibitor PDMP Sensitizes Chronic Myeloid Leukemia T315I Mutant to Bcr-AbI Inhibitor and Cooperatively Induces Glycogen Synthase Kinase-3-regulated Apoptosis," *FASEB J.* 25:3661-3673 (2011); and Todd et al., "The MAPK Pathway Functions as a Redundant Survival Signal that Reinforces the PI3K Cascade in c-Kit Mutant Melanoma," *Oncogene* Epub ahead of print (2012), which are hereby incorporated by reference in its entirety); Sorafenib (Nexavar) (see Segarra et al., "Semaphorin 6A Regulates Angiogenesis by Modulating VEGF Signaling," *Blood* 120:4104-4115 (2012); Shao et al., "BH3-only Protein Silencing Contributes to Acquired Resistance to PLX4720 in Human Melanoma," *Cell Death Differ.* 19:2029-2039 (2012); and Nicolaides et al., "Targeted Therapy for BRAFV600E Malignant Astrocytoma," *Clin. Cancer Res.* 17:7595-7604 (2011), which are hereby incorporated by reference in their entirety); Sunitinib Malate (Sutent) (see Riddell et al., "Peroxiredoxin 1 Controls Prostate Cancer Growth through Toll-like Receptor 4-dependent Regulation of Tumor Vasculature," *Cancer Res.* 71:1637-1646 (2011); van Rooijen et al., "von Hippel-lindau Tumor Suppressor Mutants Faithfully Model Pathological Hypoxiadriven Angiogenesis and Vascular Retinopathies in Zebrafish," *Dis. Model Mech.* 3:343-353 (2010); and Lin et al., "Autophagic Activation Potentiates the Antiproliferative Effects of Tyrosine Kinase Inhibitors in Medullary Thyroid Cancer," *Surgery* 152:1142-1149 (2012), which are hereby incorporated by reference in their entirety); Ponatinib (AP24534) (see Bicocca et al., "Crosstalk Between ROR1 and the Pre-B Cell Receptor Promotes Survival of t(1;19) Acute Lymphoblastic Leukemia," *Cancer Cell* 22:656-667 (2012) and Melkus et al., "Biological Effects of T315I-mutated BCR-ABL in an Embryonic Stem Cell-derived Hematopoiesis Model," *Exp. Hematol.* 41:335-345 (2013), which are hereby incorporated by reference in its entirety); BIBF1120 (Vargatef) (see Chen et al., "PDGF Signalling Controls Age-dependent Proliferation in Pancreatic β-cells," *Nature* 478:349-355 (2011); Han et al., "Inhibition of Lck Enhances Glucocorticoid Sensitivity and Apoptosis in Lymphoid Cell Lines and in Chronic Lymphocytic Leukemia," *Cell Death Differ.* 17:1381-1391 (2010), which are hereby incorporated by reference in their entirety); Axitinib (see Martin et al., "Metformin Accelerates the Growth of BRAF$^{V600E}$-driven Melanoma by Upregulating VEGF-A," *Cancer Discov.* 2:344-355 (2012); Wuestefeld et al., "Impact of VEGF on Astrocytes: Analysis of Gap Junctional Intercellular Communication, Proliferation, and Motility," *Glia.* 60:936-947 (2012); and Wang et al., "Axitinib Targeted Cancer Stemlike Cells to Enhance Efficacy of Chemotherapeutic Drugs via Inhibiting the Drug Transport Function of ABCG2," *Mol. Med.* 18:887-898 (2012), which are hereby incorporated by reference in its entirety); Crenolanib (CP-868596); Covitinib (TKI-258) (see Wasag et al., "The Kinase Inhibitor TKI258 is Active Against the Novel CUX1-FGFR1 Fusion Detected in a Patient with T-lymphoblastic Leukemia/Lymphoma and t(7;8)(q22; p11)," *Haematologica* 96:922-926 (2011); Gozgit et al., "Ponatinib (AP24534), a Multatargeted Pan-FGFR Inhibitor with Activity in Multiple FGFR-amplified or Mutated Cancer Models," *Mol. Cancer Ther.* 11:690-699 (2012); and Lamont et al., "Small Molecule FGF Receptor Inhibitors Block FGFR-dependent Urothelial Carcinoma Growth In Vitro and In Vivo," *Br. J. Cancer* 104:75-82 (2011), which are hereby incorporated by reference in their entirety); Tivozanib (AV-951); TSU-68 (SU 6668) (see Trzcinska-Daneluti et al., "Use of Kinase Inhibitors to Correct ΔF508-CFTR Function," *Mol. Cell Proteomics* 11:745-757 (2012) and Jin et al., "Positron Emission Tomography Imaging of Tumor Angiogenesis and Monitoring of Antiangiogenic Efficacy Using the Novel Tetrameric Peptide Probe (64Cu-cyclam-RAFT-c-(-RGDfK-)4," *Angiogenesis* 15:569-580 (2012), which are hereby incorporated by reference in its entirety); Masitinib (AB1010); CP673451; Linifanib (ABT-869) (see Zhong et al., "TSLP Signaling Network Revealed by SILAC-based Phosphoproteomics," *Mol. Cell Proteomics* 11:M112.017764 (2012) and Fingas et al., "Targeting PDGFR-β in Cholangiocarcinoma," *Liver Int.* 32:400-409 (2012), which are hereby incorporated by reference in their entirety); Amuvatinib (MP-470) (see Zhang et al., "Activation of the AXL Kinase Causes Resistance to EGFR-targeted Therapy in Lung Cancer," *Nat. Genet.* 44:852-860 (2012), which is hereby incorporated by reference in its entirety); MK2461; Motesanib Diphosphate (AMG-706) (see Tang et al., "VEGF/SDF-1 Promotes Cardiac Stem Cell Mobilization and Myocardial Repair in the Infarcted Heart," *Cariovasc. Res.* 91:401-411 (2011), which is hereby incorporated by reference in its entirety); Pazopanib; Dovitinib Dilactic acid (TKI258 Dilactic acid) (see Wasag et al., "The Kinase Inhibitor TKI258 is Active Against the Novel CUX1-FGFR1 Fusion Detected in a Patient with T-lymphoblastic Leukemia/Lymphoma and t(7;8)(q22;p11)," *Haematologica* 96:922-926 (2011); Gozgit et al., "Ponatinib (AP24534), a Multitargeted Pan-FGFR Inhibitor with Activity in Multiple FGFR-amplified or Mutated Cancer Models," *Mol. Cancer Ther.* 11:690-699 (2012); and Lamont et al., "Small Molecule FGF Receptor Inhibitors Block FGFR-dependent Urothelial Carcinoma Growth In Vitro and In Vivo," *Br. J. Cancer* 104:75-82 (2011), which are hereby incorporated by reference in their entirety); Ki8751 (see Hamerlik et al., "Autocrine VEGF-VEGFR2-neuropilin-1 Signaling Promotes Glioma Stem-like Cell Viability and Tumor Growth," *J. Exp. Med.* 209:507-520 (2012) and Trzcinska-Daneluti et al., "Use of Kinase Inhibitors to Correct ΔF508-CFTR Function," *Mol. Cell Proteomics* 11:745-757 (2012), which are hereby incorporated by reference in their entirety); Telatinib (BAY 57-9352); PP-121; KRN 633; Tyrphostin AG 1296 (AG1296); Pazopanib HCL (see Gorbunova et al., "VEGFR2 and Src Kinase Inhibitors Suppress Andes Virus-induced Endothelial Cell Permeability," *J. Virol.* 85:2296-2303 (2011), which is hereby incorporated by reference in its entirety); Tarceva® (erlotinib hydrochloride); TASIGNA® (nilotinib); urea derivatives as described in U.S. Patent Application Serial No. 2005/0197371 to Milanov et al., which is hereby incorporated by reference in its entirety;

SU101 (see Shawver et al., "Inhibition of Platelet-derived Growth Factor-mediated Signal Transduction and Tumor Growth by N-[4-(trifluoromethyl)-phenyl]5-methylisoxazole-4-carboxamide," *Clin. Cancer Res.* 3:1167-1177 (1997), which is hereby incorporated by reference in its entirety); SU11657 (see Cain et al., "Complete Remission of TEL-PDGFRB-induced Myeloproliferative Disease in Mice by Receptor Tyrosine Kinase Inhibitor SU11657," *Blood* 104:561-564 (2004), which is hereby incorporated by reference in its entirety); CT52923 (see Lokker et al., "Platelet-derived Growth Factor (PDGF) Autocrine Signaling Regulates Survival and Mitogenic Pathways in Glioblastoma Cells: Evidence that the Novel PDGF-C and PDGF-D Ligands May Play a Role in the Development of Brain Tumors," *Cancer Res.* 62:3729-3735 (2002), which is hereby incorporated by reference in its entirety); quinoline ether inhibitors (see Plé et al., "Discovery of New Quinoline Ether Inhibitors with High Affinity and Selectivity for PDGFR Tyrosine Kinases," *Bioorganic & Med. Chem. Lett.* 22:3050-3055 (2012), which is hereby incorporated by reference in its entirety); AZD2932 (see Plé et al., "Discovery of AZD2932, a New Quinazoline Ether Inhibitor with High Affinity for VEGFR-2 and PDGFR Tyrosine Kinases," *Bioorganic & Med. Chem. Lett.* 22:262-266 (2012), which is hereby incorporated by reference in its entirety); AC710 (see Liu et al., "Discovery of AC710, a Globally Selective Inhibitor of Platelet-derived Growth Factor Receptor-family Kinases," *ACS Med. Chem. Lett.* 3:997-1002 (2012), which is hereby incorporated by reference in its entirety); benzimidazole derivatives (see Li et al., "Discovery of Benzimidazole Derivatives as Novel Multi-target EGFR, VEGRF-2 and PDGFR Kinase Inhibitors," *Bioorganic & Med. Chem.* 19:4529-4535 (2011), which is hereby incorporated by reference in its entirety); 2-amino-4-m-bromoanilino-6-arylmethyl-7H-pyrrolo[2,3-d]pyrimidines (see Gangjee et al., "Design, Synthesis and Evaluation of 2-amino-4-m-bromoanilino-6-arylmethyl-7H-pyrrolo[2,3-d]pyrimidines as Tyrosine Kinase Inhibitors and Antiangiogenic Agents," *Bioorganic & Med. Chem.* 18:5261-5273 (2010), which is hereby incorporated by reference in its entirety); aminopyrazolopyridine ureas (see Dai et al., "Identification of Aminopyrazolopyridine Ureas as Potent VEGFR/PDFR Multitargeted Kinase Inhibitors," *Bioorganic & Med. Chem. Lett.* 18:386-390 (2008), which is hereby incorporated by reference in its entirety); bis(benzo[b]furan-2-yl)methanones (see Mahboobi et al., "Inhibition of FLT3 and PDGFR Tyrosine Kinase Activity by Bis(benzo[b]furan-2-yl)methanones," *Bioorganic & Med. Chem.* 15:2187-2197 (2007), which is hereby incorporated by reference in its entirety); 7-[3-(cyclohexylmethyl)ureido]-3-{1-methyl-1H-pyrrolo[2,3,-b]pyridine-3-yl}quinoxalin-2(1H)-one derivatives (see Aoki et al., "Potent Platelet-derived Growth Factor-β Receptor (PDGF-βR) Inhibitors: Synthesis and Structure-activity Relationships of 7-[3-(cyclohexylmethyl)ureido]-3-{1-methyl-1H-pyrrolo[2,3,-b]pyridine-3-yl}quinoxalin-2(1H)-one Derivatives," *Chem. & Pharm. Bull.* 55:255-267 (2007), which is hereby incorporated by reference in its entirety); RO4383596 (see McDermott et al., "RO4383596, an Orally Active KDR, FGFR, and PDGFR Inhibitor: Synthesis and Biological Evaluation," *Bioorganic and Med. Chem.* 13:4835-4841 (2005), which is hereby incorporated by reference in its entirety); tricyclic amine derivatives as described in PCT Publication No. WO 2008/078100 to Berdini et al., which is hereby incorporated by reference in its entirety; benzylbenzimidazolyl derivatives as described in U.S. Patent Application Publication No. 2007/0066606 to Stahle et al., which is hereby incorporated by reference in its entirety; amides as described in PCT Publication No. WO 2010/096395 to Chen, which is hereby incorporated by reference in its entirety; fused heterocyclic derivatives as described in U.S. Patent Application Publication No. 2010/0168424 to Sakai et al., which is hereby incorporated by reference in its entirety; imidazopyridazine derivatives as described in U.S. Pat. No. 8,034,812 to Sakai et al., which is hereby incorporated by reference in its entirety; and PDGFRB modulators as described in PCT Publication No. WO 2004/020583 to Turaga, which is hereby incorporated by reference in its entirety.

In another embodiment, the selected subject is administered an agent that modulates NOTCH3 gene expression and/or NOTCH3 encoded protein activity. Agents that are known to modulate NOTCH3 gene expression and/or NOTCH3 encoded protein activity include, without limitation, Semagacestat (LY450139) (see Borgegard et al., "First and Second Generation γ-secretase Modulators (GSMs) Modulate Amyloid-β(Aβ) Peptide Production through Different Mechanisms," *J. Biol. Chem.* 287:11810-11819 (2012), which is hereby incorporated by reference in its entirety); YO-01027; anti-NRR1 and anti-NRR2 antibodies (see Wu et al., "Therapeutic Antibody Targeting of Individual Notch Receptors," *Nature* 464:1052-1059 (2010), which is hereby incorporated by reference in its entirety), and the γ-secretase inhibitor MRK-003 (see Konishi et al., "γ-Secretase Inhibitor Prevents Notch3 Activation and Reduces Proliferation in Human Lung Cancers," *Cancer Res* 67:8051-8057 (2007), which is hereby incorporated by reference in its entirety).

In a further embodiment, the selected subject is administered an agent that modulates both PDGFRB and NOTCH3 gene expression and/or PDGFRB and NOTCH3 encoded protein activity.

In one embodiment of carrying out this method of the present invention, symptoms associated with infantile myofibromatosis are prevented in the selected subject. In another embodiment of the present invention, symptoms associated with infantile myofibromatosis are treated in the selected subject.

In one embodiment, the agent administered to the subject modulates mutant PDGFRB and/or NOTCH3 gene expression and/or mutant PDGFRB and/or NOTCH3 encoded protein activity. Mutations associated with infantile myofibromatosis include those described supra.

In carrying out this method, one or more anti-infantile myofibromatosis therapies are administered to the selected subject in conjunction with administering the agent that modulates PDGFRB and/or NOTCH3 gene expression and/or PDGFRB and/or NOTCH3 encoded protein activity. Suitable anti-infantile myofibromatosis therapies are described supra.

Suitable inhibitors of PDGFRB and/or NOTCH3 gene expression include nucleic acid inhibitors of PDGFRB and/or NOTCH3 gene expression, such as e.g., siRNA, shRNA, antisense molecules, microRNAs, etc. The use of antisense methods to inhibit the in vivo translation of genes and subsequent protein expression is well known in the art (see e.g., U.S. Pat. No. 7,425,544 to Dobie et al.; U.S. Pat. No. 7,307,069 to Karras et al.; U.S. Pat. No. 7,288,530 to Bennett et al.; and U.S. Pat. No. 7,179,796 to Cowsert et al., all of which are hereby incorporated by reference in their entirety). Antisense nucleic acids are nucleic acid molecules (e.g., molecules containing DNA nucleotides, RNA nucleotides, or modifications (e.g., modifications that increase the stability of the molecule, such as 2'-O-alkyl (e.g., methyl) substituted nucleotides) or combinations thereof that are complementary to, or that hybridize to, at least a portion of a specific nucleic acid molecule, such as an mRNA molecule (see e.g., Weintraub, "Antisense DNA and RNA," *Scientific Am.* 262:40-46 (1990), which is hereby incorporated by reference in its entirety). The antisense nucleic acid molecule hybridizes to its corresponding target nucleic acid molecule to form a double-stranded molecule which interferes with translation of the mRNA, as the cell will not translate a double-stranded mRNA. Antisense nucleic acids suitable for use in the methods of the present invention are typically at least 10-12 nucleotides in length or, for example, at least 15, 20, 25, 50, 75, or 100 nucleotides in length. The antisense nucleic acid can also be as long as the target nucleic acid with which it is intended to form an inhibitory duplex. Antisense nucleic acids can be introduced into cells as antisense oligonucleotides, or can be produced in a cell in which a nucleic acid encoding the antisense nucleic acid has been introduced, for example, using gene therapy methods.

siRNAs are double stranded synthetic RNA molecules approximately 20-25 nucleotides in length with short 2-3 nucleotide 3' overhangs on both ends. The double stranded siRNA molecule represents the sense and anti-sense strand of a portion of the mRNA molecule (i.e., SEQ ID NO:1 and/or SEQ ID NO:3). siRNA molecules are typically designed to target a region of the mRNA target approximately 50-100 nucleotides downstream from the start codon. Upon introduction into a cell, the siRNA complex triggers the endogenous RNA interference (RNAi) pathway, resulting in the cleavage and degradation of the target mRNA molecule.

Various improvements of siRNA compositions, such as the incorporation of modified nucleosides or motifs into one or both strands of the siRNA molecule to enhance stability, specificity, and efficacy, have been described and are suitable for use in accordance with this aspect of the present invention (see e.g., PCT Patent Application Publication WO 2004/015107 to Giese et al.; PCT Patent Application Publication WO 2003/070918 to McSwiggen et al.; PCT Patent Application Publication WO 1998/39352 to Imanishi et al.; U.S. Patent Application Publication No. 2002/0068708 to Jesper et al.; U.S. Patent Application Publication No. 2002/0147332 to Kaneko et al; and U.S. Patent Application Publication No. 2008/0119427 to Bhat et al., all of which are hereby incorporated by reference in their entirety).

Short or small hairpin RNA molecules are similar to siRNA molecules in function, but comprise longer RNA sequences that make a tight hairpin turn. shRNA is cleaved by cellular machinery into siRNA and gene expression is silenced via the cellular RNA interference pathway.

In accordance with the methods of the present invention, the mode of administering therapeutic agents, including the use of suitable delivery vehicles, to a subject will vary depending on the type of therapeutic agent (e.g., nucleic acid molecule, ribonucleoside analogue, or small molecule). For example, ribonucleoside analogues and small molecule inhibitors can be administered directly, preferably systemically. In contrast, inhibitory nucleic acid molecules (i.e., antisense, siRNA, etc.), may be incorporated into a gene therapy vector to facilitate delivery. Suitable gene therapy vectors include, without limitation, adenovirus, adeno-associated virus, retrovirus, lentivirus, or herpes virus.

Adenoviral viral vector gene delivery vehicles can be readily prepared and utilized as described in Berkner, "Development of Adenovirus Vectors for the Expression of Heterologous Genes," *Biotechniques* 6:616-627 (1988); Rosenfeld et al., "Adenovirus-Mediated Transfer of a Recombinant Alpha 1-Antitrypsin Gene to the Lung Epithelium In Vivo," *Science* 252:431-434 (1991); PCT Patent Application Publication WO 93/07283 to Curiel et al.; PCT Patent Application Publication WO 93/06223 to Perricaudet et al.; and PCT Patent Application Publication WO 93/07282 to Curiel et al., all of which are hereby incorporated by reference in their entirety.

Adeno-associated viral vector vehicles can be constructed and used to deliver inhibitory nucleic acid molecules as described by Chatterjee et al., "Dual-Target Inhibition of HIV-1 In Vitro by Means of an Adeno-associated Virus Antisense Vector," *Science* 258:1485-1488 (1992); Ponnazhagan et al., "Suppression of Human Alpha-globin Gene Expression Mediated by the Recombinant Adeno-associated Virus 2-based Antisense Vectors," *J. Exp. Med.* 179:733-738 (1994); and Zhou et al., "Adeno-Associated Virus 2-mediated Transduction and Erythroid Cell-specific Expression of a Human Beta-globin Gene," *Gene Ther.* 3:223-229 (1996), all of which are hereby incorporated by reference in their entirety. In vivo use of these vehicles is described in Flotte et al., "Stable In Vivo Expression of the Cystic Fibrosis Transmembrane Conductance Regulator With an Adeno-associated Virus Vector," *Proc. Nat'l. Acad. Sci.* 90:10613-10617 (1993) and Kaplitt et al., "Long-Term Gene Expression and Phenotypic Correction Using Adeno-associated Virus Vectors in the Mammalian Brain," *Nature Genet.* 8:148-153 (1994), both of which are hereby incorporated by reference in their entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, all of which are hereby incorporated by reference in their entirety.

Retroviral vectors which have been modified to form infective transformation systems can also be used to deliver inhibitory nucleic acid molecules to a target cell. One such type of retroviral vector is disclosed in U.S. Pat. No. 5,849,586 to Kriegler et al., which is hereby incorporated by reference in its entirety.

Gene therapy vectors carrying the therapeutic nucleic acid molecule are administered to a subject by, for example, intravenous injection or local administration (see e.g., U.S. Pat. No. 5,328,470 to Nabel et al., which is hereby incorporated by reference in its entirety). The pharmaceutical preparation of the vector can include the vector in an acceptable diluent, or can comprise a slow release matrix in which the vector delivery vehicle is imbedded. Alternatively, where the complete delivery vector can be produced intact from recombinant cells, e.g., retroviral vectors, the pharmaceutical preparation can include one or more cells which produce the gene delivery system.

The therapeutic agents of the present invention (i.e., PDGFRB and/or NOTCH3 gene expression modulating agents and or PDGFRB and/or NOTCH3 encoded protein modulating agents) can be administered via any standard route of administration known in the art, including, but not limited to, parenteral (e.g., intravenous, intraarterial, intramuscular, subcutaneous injection, intrathecal), oral (e.g., dietary), topical, transmucosal, or by inhalation (e.g., intrabronchial, intranasal or oral inhalation, or intranasal drops). Typically, parenteral administration is a preferred mode of administration.

Therapeutic agents of the present invention are formulated in accordance with their mode of administration. For oral administration, for example, the therapeutic agents are formulated into an inert diluent or an assimilable edible carrier, enclosed in hard or soft shell capsules, compressed into tablets, or incorporated directly into food. Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

Also specifically contemplated are oral dosage forms of the therapeutic agents. The agents may be chemically modified so that oral delivery of the derivative is efficacious. Generally, the chemical modification contemplated is the attachment of at least one moiety to the component molecule itself, where said moiety permits inhibition of proteolysis and uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline (see Abuchowski and Davis, "Soluble Polymer-enzyme Adducts," In Enzymes as Drugs, Hocenberg and Roberts, eds., Wiley-Interscience (1981), which is hereby incorporated by reference in their entirety). Other polymers that could be used are poly-1,3-dioxolane and poly-1,3,6-tioxocane. Preferred for pharmaceutical usage are polyethylene glycol moieties.

The therapeutic agents may also be delivered systemically, formulated for parenteral administration by injection, e.g., by bolus injection or continuous infusion. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. In all cases, the form must be sterile and must be fluid to the extent that easy syringability exists. It must be stable under the conditions of manufacture and storage and must be preserved against the contaminating action of microorganisms, such as bacteria and fungi.

Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing, and/or dispersing agents.

Intraperitoneal or intrathecal administration of the therapeutic agents can also be achieved using infusion pump devices such as those described by Medtronic (Northridge, Calif.). Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Effective doses of the therapeutic agents will vary depending upon many different factors, including type and stage of tumor, mode of administration, target site, physiological state of the patient, other medications or therapies administered, and physical state of the patient relative to other medical complications. Treatment dosages need to be titrated to optimize safety and efficacy.

A further aspect of the present invention involves diagnosing a subject as having or being a carrier for infantile myofibromatosis based on detected levels of PDGFRB and/or NOTCH3 gene expression and/or PDGFRB and/or NOTCH3 encoded protein levels and/or activity in a subject. This method involves providing an isolated biological sample from a subject; contacting the sample with one or more reagents suitable for detecting PDGFRB and/or NOTCH3 RNA and/or protein levels; detecting, in the sample, levels of PDGFRB and/or NOTCH3 RNA and/or protein based on said contacting; and diagnosing the subject as having and/or being a carrier for infantile myofibromatosis based on said detecting, where decreased levels of PDGFRB and/or NOTCH3 RNA and/or protein compared to normal levels of PDGFRB and/or NOTCH3 RNA and/or protein indicates the subject has or is a carrier for infantile myofibromatosis.

In another aspect, the present invention relates to a treatment method which involves selecting a subject having levels of PDGFRB and/or NOTCH3 gene expression and/or PDGFRB and/or NOTCH3 encoded protein levels and/or activity at a higher or lower than normal level and administering a therapy suitable for treating infantile myofibromatosis to the subject. According to one embodiment, this method involves selecting a subject having decreased levels of PDGFRB and/or NOTCH3 RNA and/or protein compared to a subject having normal levels of PDGFRB and/or NOTCH3 RNA and/or protein and administering a therapy suitable for treating infantile myofibromatosis to the selected subject.

In yet a further aspect, the present invention relates to preventing or treating symptoms associated with infantile myofibromatosis. This method involves selecting a subject having levels of PDGFRB and/or NOTCH3 gene expression and/or PDGFRB and/or NOTCH3 encoded protein levels and/or activity at a higher or lower than normal level and administering to the selected subject an agent that modulates PDGFRB and/or NOTCH3 gene expression and/or PDGFRB and/or NOTCH3 encoded protein levels and/or activity under conditions effective to prevent or treat symptoms associated with infantile myofibromatosis in the subject. According to one embodiment, this method involves selecting a subject having decreased levels of PDGFRB and/or NOTCH3 RNA and/or protein compared to a subject having normal levels of PDGFRB and/or NOTCH3 RNA and/or protein and administering to the selected subject an agent that modulates PDGFRB and/or NOTCH3 gene expression and/or PDGFRB and/or NOTCH3 encoded protein activity under conditions effective to prevent or treat symptoms associated with infantile myofibromatosis in the subject.

Yet another aspect of the present invention relates to a method of treating a subject having infantile myofibromatosis. This method involves selecting a subject having a mutation in PDGFRB encoding an amino acid substitution at one or more amino acid residues corresponding to amino acid position 561 and/or 660 of SEQ ID NO:2. The method further involves administering to the selected subject an agent that reduces phosphorylation of PDGFRB under conditions effective to prevent or treat symptoms associated with infantile myofibromatosis in the subject.

In one embodiment of carrying out these methods of the present invention, isolated biological samples from a subject are analyzed for a decrease in RNA and/or protein levels of PDGFRB and/or NOTCH3 compared to protein levels known to exist in normal (nondiseased) individuals. As would be appreciated by a person of ordinary skill in the art, certain gene mutations are known to affect the stability of the mRNA. Nonsense mediated decay is a well recognized mechanism whereby mRNA harboring mutations can be degraded by the cellular machinery. Therefore, gene mutations (most notably stop mutations) result in an absence of mRNA. This will also result in decreased/absent protein. Similarly, some mutant proteins are translated but they may not be stable. For example, their half-life could be markedly decreased resulting in degradation by the proteasome.

In one embodiment, soluble forms of PDGFRB and/or NOTCH3 encoded protein may be detected in various tissues of a subject. Assays used to detect levels of the protein in a sample derived from a subject are well known to those of ordinary skill in the art and include, without limitation, radioimmunoassays, competitive-binding assays, Western blot analysis, and ELISA assay.

An ELISA assay initially comprises preparing an antibody specific to antigens of PDGFRB and/or NOTCH3 encoded protein, preferably a monoclonal antibody. In addition, a reporter antibody is prepared against the monoclonal antibody. To the reporter antibody is attached a detectable reagent such as radioactivity or fluorescence. A sample is then removed from a host and incubated on a solid support, e.g., a polystyrene dish that binds the proteins in the sample. Any free protein binding sites on the dish are then covered by incubating with a non-specific protein such as bovine serum albumin. Next, the monoclonal antibody is incubated in the dish during which time the monoclonal antibodies attach to any PDGFRB and/or NOTCH3 encoded proteins attached to the polystyrene dish. All unbound monoclonal antibody is washed out with buffer. The reporter antibody linked to the detectable reagent is then placed in the dish resulting in binding of the reporter antibody to any monoclonal antibody bound to PDGFRB and/or NOTCH3 encoded proteins. Unattached reporter antibody is then washed out. Substrates are then added to the dish and the amount of signal developed in a given time period is a measurement of the amount of PDGFRB and/or NOTCH3 encoded protein present in a given volume of patient sample when compared against a standard curve.

EXAMPLES

The following examples are provided to illustrate embodiments of the present invention but are by no means intended to limit its scope.

Subjects and Methods for Example 1

Subjects

After informed consent and Institutional Review Board approval from the Icahn. School of Medicine of Mount Sinai and the corresponding institutions were obtained, blood samples were obtained from 32 affected individuals, from nine unrelated families with the diagnosis of IM and, where possible, unaffected family members. Clinical diagnoses were provided by the referring physicians. Genomic DNA was extracted with the Puregene kit according to the manufacturer's protocol (Minneapolis, Minn.). Cell lines were established from tumor tissue that was removed from affected individuals as part of their medical care and which was considered pathologic waste.

Whole-exome Capturing and Sequencing

One unaffected and 11 affected family members, representing nine unrelated kindred, were selected for whole-exome sequencing at the Center for Applied Genomics at The Children's Hospital of Philadelphia. Genomic DNA was isolated from a blood sample by standard methods and randomly sheared to 200-300 bp in size, followed by end-repair, A-tailing, and paired-end index adapter ligation. Whole-exomes were captured using the Agilent SureSelect Human All Exon V4+UTR kit (Agilent Technologies, Santa Clara, Calif., USA) following the manufacturer's protocol. The libraries were subsequently clustered on the cBOT instrument, multiplexing 4 samples per flow cell lane, and sequenced for 101 cycles using a paired-end mode on the Illumina HiSeq2000 following the manufacturer's instructions (Illumina, San Diego, Calif., USA). Base calling and index demultiplexing was performed with the Illumina CASAVA software (version 1.8.2).

Variant Analysis

Sequencing reads were aligned to the human reference genome (UCSC hg19) with Burrows-Wheeler Aligner (BWA, version 0.6.2) (Li et al., "Fast and Accurate Short Read Alignment with Burrows-wheeler Transform," *Bioinformatics* 25:1754-1760 (2009), which is hereby incorporated by reference in its entirety). Optical and PCR duplicates were marked and removed with Picard (version 1.73). Local realignment of reads containing indel sites and base quality score recalibration (BQSR) were performed with the Genome Analysis Tool Kit (GATK, version 2.3) (DePristo et al., "A Framework for Variation Discovery and Genotyping Using Next-generation DNA Sequencing Data," *Nature Genetics* 43:491-498 (2011), which is hereby incorporated by reference in its entirety). Single nucleotide variation ("SNV") and small indels were called with GATK UnifiedGenotyper. Variants were marked as potential sequencing artifacts if the filters on the following annotations were evaluated to be true: (i) for SNVs, "DP<10", "QD<2.0", "MQ<40.0", "FS>60.0", "HaplotypeScore >13.0", "MQRankSum <−12.5", "ReadPosRankSum <−8.0" and (ii) for small indels, "DP<10", "QD<2.0", "ReadPosRankSum <−20.0", "InbreedingCoeff <−0.8", "FS>200.0". The kinship coefficient was calculated for each sample using KING (Manichaikul et al., "Robust Relationship Inference in Genome-wide Association Studies," *Bioinformatics* 26:2867-2873 (2010), which is hereby incorporated by reference in its entirety) to confirm reported relationships and identify cryptic relationships among samples. ANNOVAR (Wang et al., "ANNOVAR: Functional Annotation of Genetic Variants from Next-generation Sequencing Data," *Nucleic Acids Research* 38:e164 (2010), which is hereby incorporated by reference in its entirety) and SnpEff (version 2.0.5) (Cingolani et al., "A Program for Annotating and Predicting the Effects of Single Nucleotide Polymorphisms, SnpEff: SNPs in the Genome of *Drosophila melanogaster* Strain w1118; iso-2; iso-3," *Fly* 6:2 (2012), which is hereby incorporated by reference in its entirety) were used for annotating variants. Human Gene Mutation Database (HGMD) (Stenson et al., "The Human Gene Mutation Database (HGMD): 2008 Update," *Genome Med.* 1:13 (2009), which is hereby incorporated by reference in its entirety) was used for annotating known genes and mutations for human inherited diseases. Prediction scores from SIFT (Kumar et al., "Predicting the Effects of Coding Non-synonymous Variants on Protein Function Using the SIFT Algorithm," *Nat. Protoc.* 4:1073-1081 (2009), which is hereby incorporated by reference in its entirety), Polyphen2 (Adzhubei et al., "A Method and Server for Predicting Damaging Missense Mutations," *Nat. Methods* 7:248-249

(2010), which is hereby incorporated by reference in its entirety), LRT (Chun et al., "Identification of Deleterious Mutations Within Three Human Genomes," *Genome Res.* 19:1553-1561 (2009), which is hereby incorporated by reference in its entirety), and MutationTaster (Schwarz et al., "Mutation Taster Evaluates Disease-causing Potential of Sequence Alterations," *Nat. Methods* 7:575-576 (2010), which is hereby incorporated by reference in its entirety), along with conservation scores PhyloP (Siepel et al., "New Methods for Detecting Lineage-specific Selection," *Proceedings of the 10th International Conference on Research in Computational Molecular Biology (RECOMB* 2006) pp. 190-205 (2006), which is hereby incorporated by reference in its entirety) and GERP++ (Davydov et al., "Identifying a High Fraction of the Human Genome to be Under Selective Constraint Using GERP++," *PLoS Comput. Biol.* 6:e1001025 (2010), which is hereby incorporated by reference in its entirety) for every potential nonsynonymous SNV in the human genome were retrieved from dbNSFP (database for nonsynonymous SNPs' functional predictions) (Liu et al., "dbNSFP: A Lightweight Database of Human Non-synonymous SNPs and Their Functional Predictions," *Hum. Mutat.* 32:894-899 (2011), which is hereby incorporated by reference in its entirety). SNVs and indels were selected as potential pathogenic variants if they met all the following criteria: (i) heterozygous; (ii) not previously described or rare (minor allele frequency (MAF)<0.5%) in a control cohort of more than 9000 control individuals (1000 genomes project, April 2012 release; 6503 exomes from NHLBI GO Exome Sequencing Project (ESP6500SI), and 1200 in-house whole-exomes; (iii) nonsynonymous, or splice acceptor and donor site SNVs, or frameshift coding indels (NS/SS/I); (iv) predicted to be deleterious by at least 3 prediction methods, i.e., SIFT, PolyPhen2, MutationTaster, and LRT; and (v) conserved PhyloP score and GERP++score >2.0. Variants were also analyzed using the Ingenuity Variant Analysis webbased application.

Sanger Sequencing Validation

Sanger sequencing of the variants was performed with ABI BigDye Terminator Cycle Sequencing Kit on an ABI 3730 sequencer. It was performed using the standard techniques of PCR amplicons with the following primers:

```
(i) c.4556T > C (p.Leu1519Pro) in NOTCH3
(RefSeq NM_000435):
                                  (SEQ ID NO: 5)
5'-GTCACTCACCCGATCACCTC-3'
and
                                  (SEQ ID NO: 6)
5'-AGCCCGGTGTACGAGAAGTA-3';

(ii) c.1978C > A (p.Pro660Thr) in PDGFRB
(RefSeq NM_002609):
                                  (SEQ ID NO: 7)
5'-CTCCCACGTGGAGTCATAGG-3'
and
                                  (SEQ ID NO: 8)
5'-TGTCCTAGACGGACGAACCT-3';

(iii) c.1681C > T (p.Arg561Cys) in PDGFRB
(RefSeq NM_002609):
                                  (SEQ ID NO: 9)
5'-CAGCAGGAGTGTGCTGTTGT-3'
and
                                  (SEQ ID NO: 10)
5'-CGGGGCAGAAGAGTCAGAAT-3'.
```

Cell Culture

Cells were maintained in complete media: DMEM-F12 (Invitrogen) with 10% FBS (Atlanta Biologicals) with ABAM and Gentamicin (Sigma). For immunocytochemistry cells were plated on 10 µg/ml collagen in supplemented serum-free media (SSFM): DMEM-F12 plus RPMI-1640 Vitamin Mix, ITS Liquid media supplement, 1 mg/ml glutathione; 2 mM L-glutamine, 1 mM sodium pyruvate, 0.1 mM MEM non-essential amino acids; with ABAM and Gentamicin (Ng et al., "Exome Sequencing Identifies the Cause of a Mendelian Disorder," *Nat. Genet.* 42:30-35 (2010), which is hereby incorporated by reference in its entirety).

Immunocytochemistry

Cells were fixed with 3% p-formaldehyde (Fisher Scientific, Fair Lawn, N.J.) and permeabilized with 0.1% Triton X-100 (Sigma). After blocking with 3% normal mouse serum (Jackson Immuno Research), cells were incubated with vimentin antibody (rabbit) and a-SMA antibody (mouse) (Sigma) followed by secondary antibodies-Alexa 488 (vimentin) or Alexa-568 (a-SMA). Coverslips were viewed with a Zeiss Axioskop microscope and images were captured using a Zeiss Axioscope with a SPOT-2 CCD camera (Diagnostic Instruments, Sterling Heights, Mich.) and processed by Adobe PhotoShop software).

Example 1

Exome Sequencing Identifies Mutations in PDGFRB and NOTCH3 as Causes of Autosomal Dominant Infantile Myofibromatosis Results Exome capturing and sequencing was originally performed on nine probands from the nine unrelated IM families (FIG. 1). Agilent SureSelect was used to prepare libraries for paired-end sequencing (2×101 bp) on Illumina HiSeq 2000 sequencers. On average, 9.7 Gb of sequences were produced for each sample. 97% of the reads were mappable to the human reference genome (hg19), and 94% of targeted exome had at least 10× depth of coverage. The mean depth of coverage was 74-fold.

Figure 2:
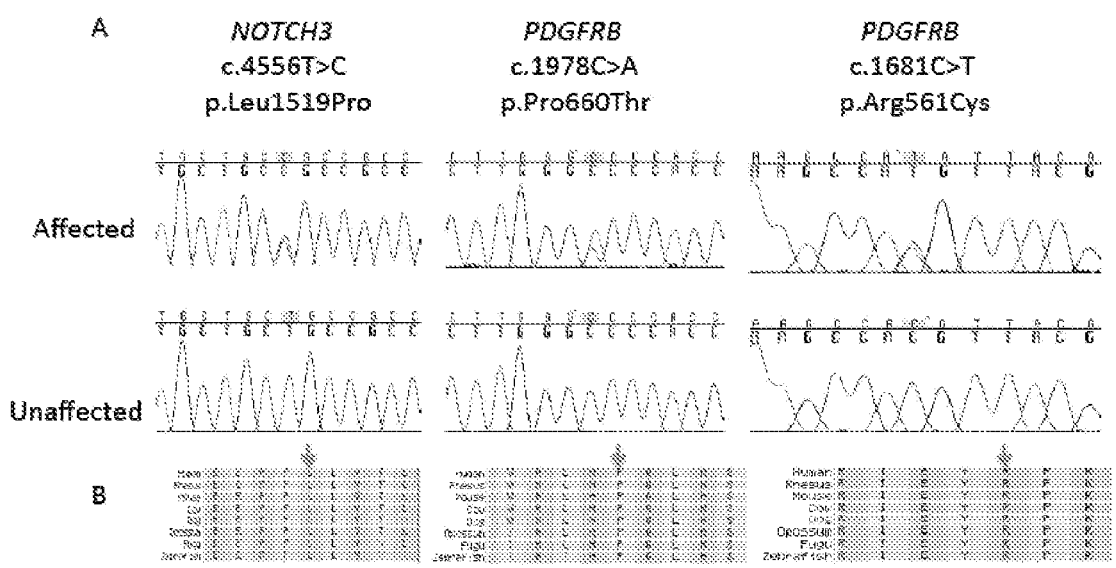
FIGS. 2A-B relate to the identification of mutations in PDGFRB and NOTCH3.
Figure 4:
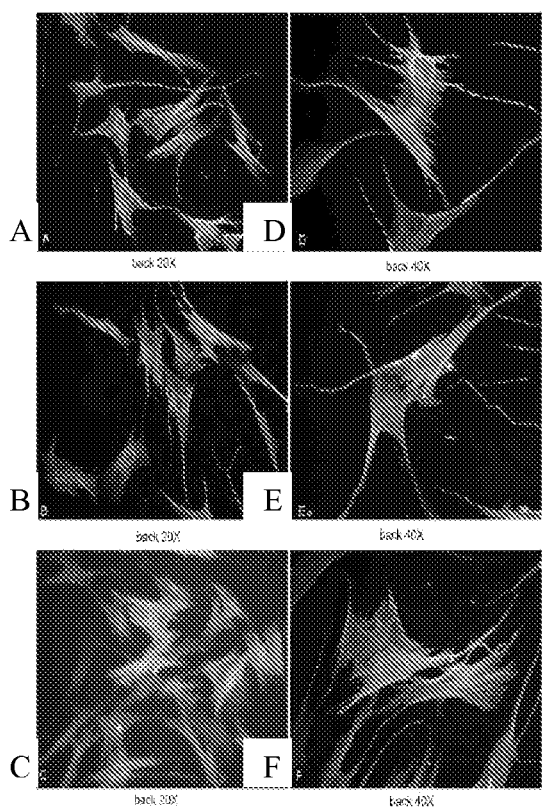
FIGS. 4A-F are photographs illustrating patient-derived tumor cell lines that demonstrate a myofibroblastic phenotype. Illustrated are vimentin and α-SMA staining of patient-derived tumor cell lines from family 9. Cells were cultured from a soft-tissue tumor excised from an affected area on the patient's back as part of their care. Three paired 20× (FIGS. 4A-C) and 40× (FIGS. 4D-F) views are shown.
Figures 5, 6:
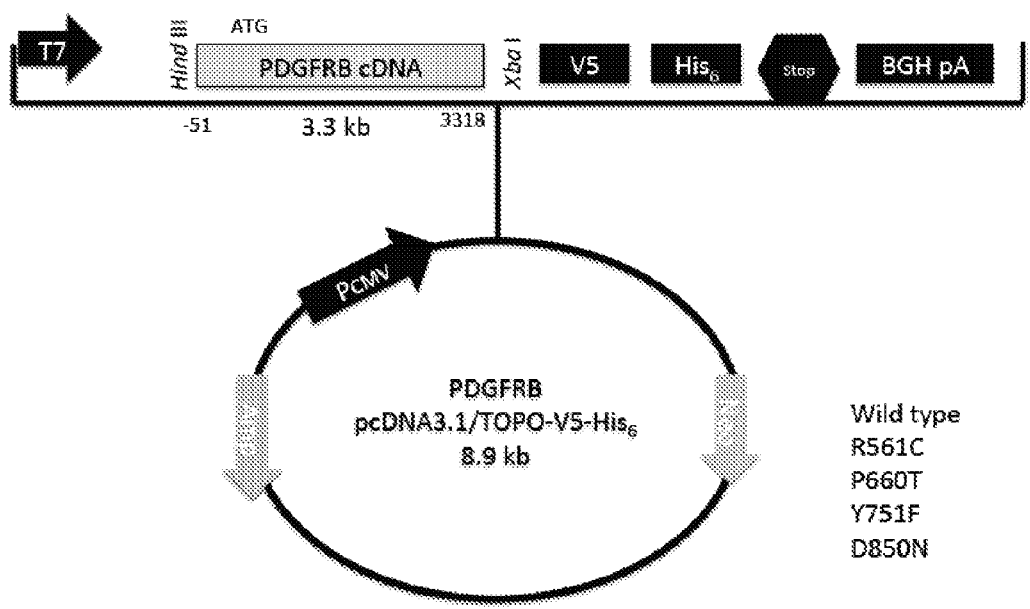
FIG. 5 is a table showing rare variants in PDGFRB and NOTCH3 identified in 9 IM families for WES.
FIG. 6 is a schematic illustration of the transient expression plasmid pcDNA3.1/TOPO-V5-His$_6$ for expression PDGFRB clones.

A total of 195,651 SNVs and 20,700 indels were identified, of which 178,991 SNVs (91%) and 17,238 indels (83%) were reported in dbSNP135. On average, 82,855 SNVs and 11,882 indels were called per sample. The filtering strategy was applied to focus on a subset of potentially pathogenic variants (Ng et al., "Exome Sequencing Identifies the Cause of a Mendelian Disorder," *Nat. Genet.* 42:30-35 (2010), which is hereby incorporated by reference in its entirety). Variants were filtered by mode of inheritance, variant quality, conservation, predicted deleterious scores, and allele frequency in the public and in-house whole exomes. Two missense variants in PDGFRB (MIM 173410; NM 002609.3, which are hereby incorporated by reference in their entirety) were present in eight members in eight families. No PDGFRB mutations were identified in family 9 (FIG. 5). Sanger sequencing of all available family members, affected and unaffected, in the eight families revealed that the two PDGFRB variants segregated appropriately with disease status (FIG. 2). In family IM-9, in which no PDGFRB mutations were identified, two other affected and one unaffected individual from this kindred were exome sequenced. Variants in NOTCH3 (MIM 600276; NM_000435.2, which are hereby incorporated by reference in their entirety) and PET112 (MIM 603645; NM_004564.2, which are hereby incorporated by reference in their entirety) were found in all three affected members but not in the unaffected family member (FIG. 5). Sanger sequencing of 16 family members, consisting of nine affected and seven unaffected individuals, revealed that only the NOTCH3 mutation c.4556T>C (p.Leu1519Pro) segregated appropriately with affected status (FIG. 2). Given the unexpected finding of candidate disease-causing mutations in a second gene, the histologic findings were re-examined in a soft tissue tumor isolated from this family and also a cell line was generated from affected tissue (Wang et al., "Degradation of Internalized avb5 Integrin is Controlled by uPAR Bound uPA: Effect on b1 Integrin Activity and α-SMA Stress Fiber Assembly," *PLoS One* 7:e33915 (2012), which is hereby incorporated by reference in its entirety). Histopathologic analysis was consistent with the diagnosis of IM and staining with α-SMA further demonstrated the tumor's myofibroblastic nature (FIG. 4).

All three rare missense variants in both genes were predicted to be damaging with high probability using the prediction algorithms LRT, MutationTaster, Polyphen2, and SIFT and they were located in highly conserved exonic regions. In PDGFRB, c.1978C>A (p.Pro660Thr) is a heterozygous missense variant in exon 14. It is located in the tyrosine kinase domain of the protein. The variant was present in the ESP6500SI dataset with a MAF of 0.000077. It was reported in dbSNP135 (rs144050370), but was not found in the 1000 genomes project, the catalogue of somatic mutations in cancer (COSMIC v63), nor in a database of approximately 1200 in-house sequenced whole-exomes. The second PDGFRB variant, c.1681C>T(p.Arg561Cys), is a heterozygous missense variant in exon 12. It is not present in the publically available databases nor in the approximately 9000 public and in-house whole-exome datasets. For family IM-9, the NOTCH3 variant C.4556T>C (p.Leu1519Pro) predicts a heterozygous missense variant in exon 25. It is a newly described variant, not present in public databases and in-house whole-exomes. It is located in the protein's highly conserved hetero-dimerization domain.

Discussion

By exome sequencing, three missense mutations have been identified in two genes causing autosomal dominant IM in nine unrelated families, i.e., c.1978C>A (p.Pro660Thr) and c.1681C>T (p.Arg561Cys) in PDGFRB, and c.4556T>C (p.Leu1519Pro) in NOTCH3 (FIG. 3).

In the current study, two missense mutations in PDGFRB were identified in eight IM families. PDGFRB, located on 5q32, encodes the platelet-derived growth factor receptor-beta. It is a cell surface tyrosine kinase receptor for members of the platelet-derived growth factor family (PDGF A, B, C, and D), which are mitogens for cells of mesenchymal origin. Activation of the receptor leads to its dimerization, autophosphorylation of tyrosine residues, and to activation of downstream signaling pathways, inducing cellular proliferation, differentiation, survival, and migration. PDGFRB is expressed in neurons, plexus choroideus, vascular smooth muscle cells (VSMCs), and pericytes. PDGFRB signal transduction is required for proliferation and migration of a subset of VSMCs. PDGFRB signaling has been well established in early hematopoiesis and blood vessel formation (Demoulin et al., "Platelet-derived Growth Factors and Their Receptors in Normal and Malignant Hematopoiesis," *Am. J. Blood. Res.* 2:44-56 (2012), which is hereby incorporated by reference in its entirety). Enhanced PDGF-PDGFR signaling is a hallmark in a variety of diseases, including cancers, atherosclerosis, pulmonary fibrosis, and restenosis. Recently, a missense mutation, c.1973T>C (p.Leu658Pro) in PDGFRB, was reported to be a recently identified cause of idiopathic basal ganglia calcification (IBGC) (Nicolas et al., "Mutation of the PDGFRB Gene as a Cause of Idiopathic Basal Ganglia Calcification," *Neurology* 80:1-7 (2013), which is hereby incorporated by reference in its entirety).

One novel missense mutation c.4556T>C (Leu1519Pro) in NOTCH3 was identified as the most probable causative mutation for one IM family. NOTCH3 encodes the third discovered human homologue of the *Drosophila melanogaster* type I membrane protein notch. Notch signaling allows cells to coordinate fate decisions in metazoan development. Notch signals are highly pleiotropic, dictating cellular fates in a way that depends on cellular context. NOTCH3 is primarily expressed in adult arterial vascular smooth muscle cells (VSMCs) in large conduit, pulmonary, and systemic resistance arteries. Mutations in NOTCH3 have also been identified as the underlying cause of cerebral autosomal dominant arteriopathy with subcortical infarcts and leukoencephalopathy (CADASIL) (Joutel et al., "Notch3 Mutations in CADASIL, a Hereditary Adult-onset Condition Causing Stroke and Dementia," *Nature* 383:707-710 (1996), which is hereby incorporated by reference in its entirety). The NOTCH3 IM family members are notable for possessing multiple, recurrent soft tissue lesions and have no reported clinical history consistent with a diagnosis of CADASIL. The majority of reported CADASIL-associated mutations are located in the epidermal growth factor-like (EGF-like) domain in the extra-cellular domain of the protein (exons 2-24). A novel heterozygous missense mutation (c.4544T>C, p.Leu1515Pro) was recently reported in exon 25, a highly conserved hetero-dimerization domain of Notch3, in a patient with cerebral small-vessel-disease but lacking typical deposits and Notch3 accumulation (Fouillade et al., "Activating NOTCH3 Mutation in a Patient with Small-vessel-disease of the Brain," *Hum. Mutat.* 29:452 (2008), which is hereby incorporated by reference in its entirety). Biochemical analysis suggests that the c.4544T>C (p.Leu1515Pro) mutation renders Notch3 hyperactive through destabilization of the heterodimer. The novel mutation c.4556T>C (p.Leu1519Pro) identified in an IM family was located close to the Leu1515Pro substitution.

Of particular interest in trying to understand how mutations in two different genes, PDGFRB and NOTCH3, could result in the same disease, a possible mechanistic link was recently provided (Jin et al., "Notch Signaling Regulates Platelet-derived Growth Factor Receptor-beta Expression in Vascular Smooth Muscle Cells," *Circ. Res.* 102:1483-1491 (2008), which is hereby incorporated by reference in its entirety). Specifically, it was demonstrated that PDGFRB was a previously unrecognized and immediate Notch3 target gene (Jin et al., "Notch Signaling Regulates Platelet-derived Growth Factor Receptor-beta Expression in Vascular Smooth Muscle Cells," *Circ. Res.* 102:1483-1491 (2008), which is hereby incorporated by reference in its entirety). PDGFRB expression was upregulated by Notch3 ligand induction or by activated forms of the Notch3 receptor. The availability of established tumor cell lines from patients will allow direct exploration of this mechanistic link. In view of the IM disease-causing mutations in PDGFRB and NOTCH3 demonstrated herein, modulation of PDGFRB and/or NOTCH3 provide a targeted therapeutic strategy.

In conclusion, these studies indicate that PDGFRB mutations are a case of autosomal dominant IM, a genetically heterogeneous disease with incomplete penetrance and variable expressivity. These studies have also identified a single family with a germline NOTCH3 mutation.

Example 2

Transient Expression of Mutant PDGFRB

PDGFRB cDNAs were cloned into transient expression plasmid pcDNA3.1/TOPO-V5-His$_6$ (FIG. 6) to produce wildtype clones, IMF-causing clones (i.e., R561C and P660T mutants), and loss-of-function PDGFRB mutant Y751F and gain-of-function PDGFRB mutant D850N.

Cloning was carried out in COST cells using the XtremeGene transfection reagent, 1 μg of DNA and 3 μg of reagent per one 6-well plate well. Cells were incubated for 24-48 hours. Cells were starved with serum-free medium for 17 hours. Cells were stimulated with PDGF-BB (50 ng/ml) for 30 minutes. Cell pellets were collected. Cells were then lysed.

Figure 7:
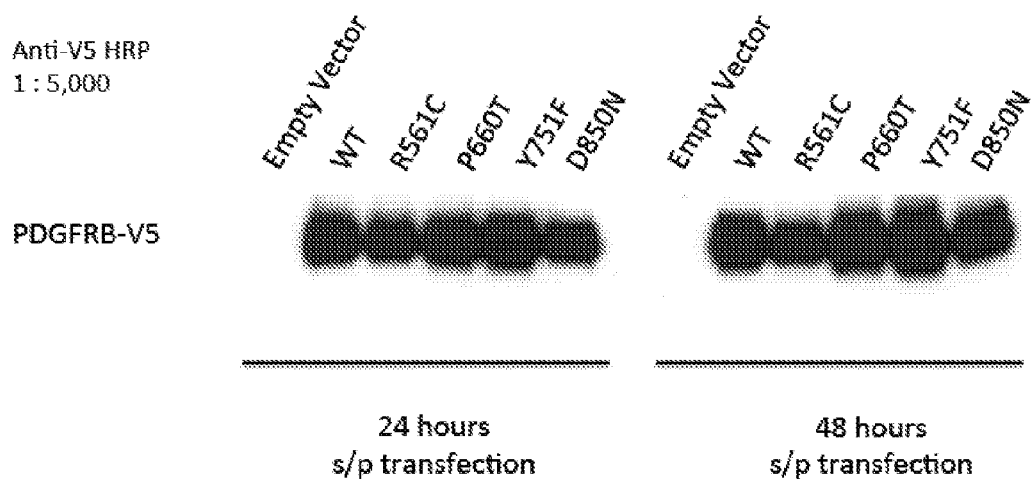
FIG. 7 is a photograph of results of an expression study carried out to detect V5 tagged protein.

An expression study was carried out to detect V5 tagged protein, the results of which are illustrated in FIG. 7.

Figure 8A:
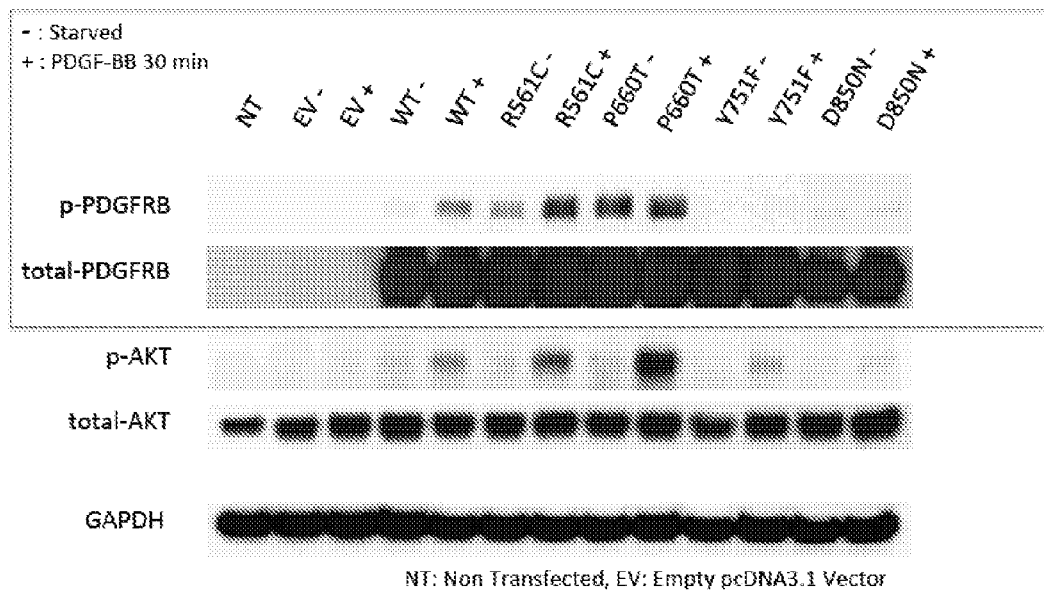
FIGS. 8A and 8B illustrate results using anti-p-PDGFRB and anti-pAKT antibodies. In a transient expression system, the two PDGFRB mutations are activating mutations, which result in autophosphorylation of PDGFRB, in the absence of PDGF-BB.
Figure 8B:
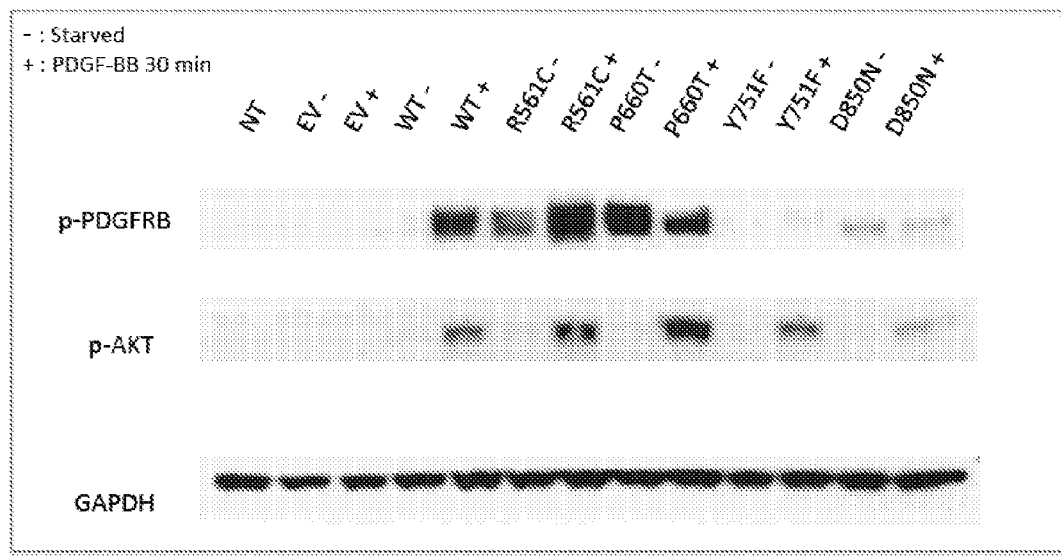

Results using anti-PDGFRB, anti-p-PDGFRB, and anti-pAKT antibodies are set forth in FIGS. 8A-B. In a transient expression system, the two PDGFRB mutations described herein are activating mutations, which result in autophosphorylation of PDGFRB, in the absence of PDGF-BB.

Example 3

Treatment with Imatinib Blocks Activation of IMF Gain-of-Function Mutants

Transient expression of PDGFRB mutants was carried out using plasmid pcDNA3.1/TOPO-V5-His$_6$, as described supra.

Figure 9:
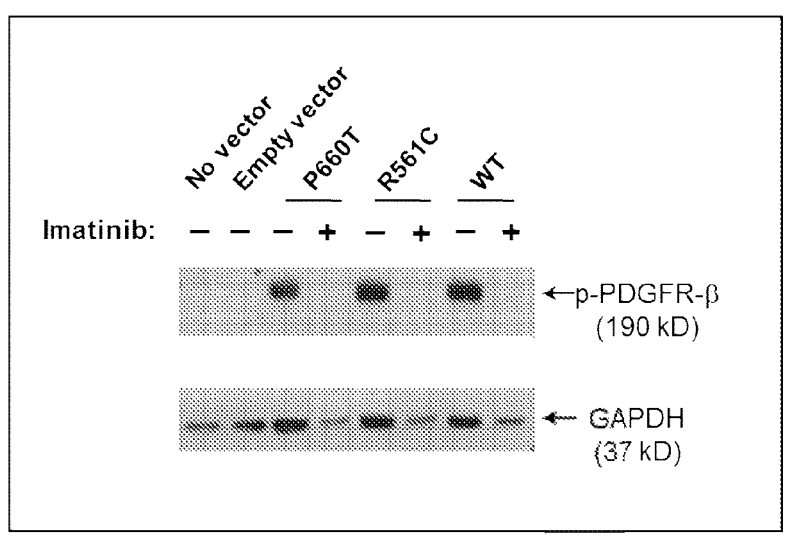
FIG. 9 is a photograph showing results of treatment with Imatinib, which demonstrates that Imatinib blocks activation of IMF gain-of-function mutants.

Treatment with Imatinib was shown to block activation of IMF gain-of-function mutants. Specifically, Imatinib (Selleckchem) was prepared to a 10 mM stock by dissolving dH$_2$O and filtering through a 0.22 μm filter. PDGFRB from Cell Signaling was used at 1:1000 overnight incubation. Lysates were collected 7.5 hours after treatment with 10 μm Imatinib. 50 μg of lysate was loaded on gels for electrophoresis/Western blotting. Results are shown in FIG. 9. The antibodies used in the Western to image p-PDGFRB and PDGFRB were Phospho-PDGF Receptor beta (Tyr751) (C63G6) Rabbit mAB #4549 and PDGF Receptor beta (28E1) Rabbit mAb #3169, respectively. These results indicate that Gleevec was able to reduce the phosphorylation of PDGFRB for both the mutants and wt PDGFRB.

All of the features described herein (including any accompanying claims, abstract and drawings), and/or all of the steps of any method or process so disclosed, may be combined with any of the above aspects in any combination, except combinations where at least some of such features and/or steps are mutually exclusive.

What is claimed:

1. A method of treating a subject having one or more missense mutations in PDGFRB and/or NOTCH, said method comprising:
   providing an isolated biological sample from a subject;
   contacting the sample with one or more reagents suitable for detecting the presence of one or more missense mutations in PDGFRB and/or NOTCH3;
   detecting, in the sample, the presence of the one or more mutations in PDGFRB and/or NOTCH3 based on said contacting; and
   administering a therapy suitable for treatment of infantile myofibromatosis to a subject identified as having one or more mutations in PDGFRB and/or NOTCH3.

2. The method according to claim 1, wherein the biological sample comprises a blood sample.

3. The method according to claim 1, wherein the one or more mutations is in PDGFRB and encode an amino acid substitution at one or more amino acid residues corresponding to amino acid position 561 and/or 660 of SEQ ID NO:2, and the one or more mutations in NOTCH3 encode an amino acid substitution at an amino acid residue corresponding to amino acid position 1519 of SEQ ID NO:4.

4. The method according to claim 3, wherein the amino acid substitution in NOTCH3 comprises a leucine to proline substitution at the amino acid position corresponding to Leu1519 of SEQ ID NO:4.

5. The method according to claim 1, wherein said detecting comprises sequencing at least a portion of a nucleotide sequence in the sample corresponding to PDGFRB and/or NOTCH3.

6. The method according to claim 1, wherein said detecting comprises:
   carrying out a hybridization assay with one or more oligonucleotide probes having a nucleotide sequence that is complementary to a nucleotide sequence of a nucleic acid molecule in a sample comprising the one or more mutations in PDGFRB and/or NOTCH3.

7. The method according to claim 1, wherein said detecting comprises carrying out an amplification-based assay with one or more oligonucleotide primers suitable for hybridization to and amplification of a nucleic acid molecule comprising the one or more mutations in PDGFRB and/or NOTCH3.

8. A method of treating a subject having infantile myofibromatosis, said method comprising:
   selecting a subject having one or more missense mutations in PDGFRB and/or NOTCH3 and
   administering an agent that modulates mutant PDGFRB and/or NOTCH3 gene expression and/or mutant PDGFRB and/or NOTCH3 encoded protein activity to the selected subject thereby treating infantile myofibromatosis.

9. The method according to claim 8, wherein the one or more mutation in PDGFRB encodes an amino acid substitution at one or more amino acid residue corresponding to amino acid position 561 and/or 660 of SEQ ID NO:2, and the one or more mutation in NOTCH3 encodes an amino acid substitution at an amino acid residue corresponding to amino acid position 1519 of SEQ ID NO:4.

10. The method according to claim 9, wherein the amino acid substitution in NOTCH3 comprises a leucine to proline substitution at the amino acid position corresponding to Leu1519 of SEQ ID NO:4.

11. A method of preventing or treating symptoms associated with infantile myofibromatosis comprising:
   (i) selecting a subject having decreased levels of PDGFRB and/or NOTCH3 RNA and/or protein compared to a subject having normal levels of PDGFRB and/or NOTCH3 RNA and/or protein, or selecting a subject having one or more mutations in PDGFRB and/or NOTCH3; and
   (ii) administering to the selected subject an agent that modulates PDGFRB and/or NOTCH3 gene expression and/or PDGFRB and/or NOTCH3 encoded protein activity under conditions effective to prevent or treat symptoms associated with infantile myofibromatosis in the subject.

12. The method according to claim 11, wherein the agent modulates mutant PDGFRB and/or NOTCH3 gene expression and/or mutant PDGFRB and/or NOTCH3 encoded protein activity.

13. The method according to claim 11, wherein the one or more mutation in PDGFRB encodes an amino acid substitution at one or more amino acid residues corresponding to amino acid position 561 and/or 660 of SEQ ID NO:2, and wherein the one or more mutation in NOTCH3 encodes an amino acid substitution at an amino acid residue corresponding to amino acid position 1519 of SEQ ID NO:4.

14. The method according to claim 13, wherein the amino acid substitution in NOTCH3 comprises a leucine to proline substitution at the amino acid position corresponding to Leu1519 of SEQ ID NO:4.

15. The method according to claim 1, wherein the one or more reagents suitable for detecting the presence of one or more mutations in PDGFRB and/or NOTCH3 comprise an antibody.

16. The method of claim 8, wherein the agent is imatinib.

17. The method of claim 1, wherein the therapy is selected from the group consisting of removal of a tumor, administering radiation therapy, and modulating PDGFRB and/or NOTCH3 gene expression and/or PDGFRB and/or NOTCH3 encoded protein activity.

18. The method of claim 11, wherein the agent is Imatinib, Covitinib (TKI-258), Linifanib (ABT-869), and Motesanib Diphosphate (AMG-706).

19. The method of claim 11, wherein the method comprises treating symptoms.

20. The method according to claim 3, wherein the amino acid substitution in PDGFRB comprises an arginine to cysteine substitution at the amino acid position corresponding to Arg561 of SEQ ID NO: 2.

21. The method according to claim 3, wherein the amino acid substitution in PDGFRB comprises a proline to threonine substitution at the amino acid position corresponding to Pro660 of SEQ ID NO: 2.

22. The method according to claim 9, wherein the amino acid substitution in PDGFRB comprises an arginine to cysteine substitution at the amino acid position corresponding to Arg561 of SEQ ID NO: 2.

23. The method according to claim 9, wherein the amino acid substitution in PDGFRB comprises a proline to threonine substitution at the amino acid position corresponding to Pro660 of SEQ ID NO: 2.

* * * * *

SEQUENCE LISTING

```
<160> NUMBER OF SEQ ID NOS: 10

<210> SEQ ID NO 1
<211> LENGTH: 5718
<212> TYPE: DNA
<213> ORGANISM: Homo sapiens

<400> SEQUENCE: 1
ctcctgaggc tgccagcagc cagcagtgac tgcccgccct atctgggacc caggatcgct      60
ctgtgagcaa cttggagcca gagaggagat caacaaggag gaggagagag ccggcccctc     120
agccctgctg cccagcagca gcctgtgctc gccctgccca acgcagacag ccagacccag     180
ggcggcccct ctggcggctc tgctcctccc gaaggatgct tggggagtga ggcgaagctg     240
ggccgctcct ctcccctaca gcagcccct tcctccatcc ctctgttctc ctgagccttc     300
aggagcctgc accagtcctg cctgtccttc tactcagctg ttacccactc tgggaccagc     360
agtctttctg ataactggga gagggcagta aggaggactt cctggagggg gtgactgtcc     420
agagcctgga actgtgccca caccagaagc catcagcagc aaggacacca tgcggcttcc     480
gggtgcgatg ccagctctgg ccctcaaagg cgagctgctg ttgctgtctc tcctgttact     540
tctggaacca cagatctctc agggcctggt cgtcacaccc ccggggccag agcttgtcct     600
caatgtctcc agcaccttcg ttctgacctg ctcgggttca gctccggtgg tgtgggaacg     660
gatgtcccag gagcccccac aggaaatggc caaggcccag gatggcacct tctccagcgt     720
gctcacactg accaacctca ctgggctaga cacgggagaa tacttttgca cccacaatga     780
ctcccgtgga ctggagaccg atgagcggaa acggctctac atctttgtgc cagatcccac     840
cgtgggcttc ctccctaatg atgccgagga actattcatc tttctcacgg aaataactga     900
gatcaccatt ccatgccgag taacagaccc acagctggtg gtgacactgc acgagaagaa     960
agggacgttg cactgcctg tcccctatga tcaccaacgt ggcttttctg gtatctttga    1020
ggacagaagc tacatctgca aaaccaccat tggggacagg gaggtggatt ctgatgccta    1080
ctatgtctac agactccagg tgtcatccat caacgtctct gtgaacgcag tgcagactgt    1140
ggtccgccag ggtgagaaca tcacccctca tgtgcattgt g atcgggaatg aggtggtcaa    1200
```

```
cttcgagtgg acatacccccc gcaaagaaag tgggcggctg gtggagccgg tgactgactt    1260
cctcttggat atgccttacc acatccgctc catcctgcac atccccagtg ccgagttaga    1320
agactcgggg acctacacct gcaatgtgac ggagagtgtg aatgaccatc aggatgaaaa    1380
ggccatcaac atcaccgtgg ttgagagcgg ctacgtgcgg ctcctgggag aggtgggcac    1440
actacaattt gctgagctgc atcggagccg gacactgcag gtagtgttcg aggcctaccc    1500
accgcccact gtcctgtggt tcaaagacaa ccgcaccctg ggcgactcca cgcctggcga    1560
aatcgccctg tccacgcgca acgtgtcgga gacccggtat gtgtcagagc tgacactggt    1620
tcgcgtgaag gtggcagagg ctggccacta ccatgcgg gccttccatg aggatgctga    1680
ggtccagctc tccttccagc tacagatcaa tgtccctgtc cgagtgctgg agctaagtga    1740
gagccaccct gacagtgggg aacagacagt ccgctgtcgt ggccgggca tgccccagcc    1800 gaacatcatc tggtctgcct gcagagacct caaaaggtgt ccacgtgagc tgccgcccac    1860
gctgctgggg aacagttccg aagaggagag ccagctggag actaacgtga cgtactggga    1920
ggaggagcag gagtttgagg tggtgagcac actgcgtctg cagcacgtgg atcggccact    1980
gtcggtgcgc tgcacgctgc gcaacgctgt gggccaggac acgcaggagg tcatcgtggt    2040
gccacactcc ttgcccttta aggtggtggt gatctcagcc atcctggccc tggtggtgct    2100
caccatcatc tccccttatca tcctcatcat gctttggcag aagaagccac gttacgagat    2160
ccgatggaag gtgattgagt ctgtgagctc tgacggccat gagtacatct acgtggaccc    2220
catgcagctg ccctatgact ccacgtggga gctgccgcgg gaccagcttg tgctgggacg    2280
caccctcggc tctggggcct ttgggcaggt ggtggaggcc acggctcatg gcctgagcca    2340
ttctcaggcc acgatgaaag tggccgtcaa gatgcttaaa tccacagccc gcagcagtga    2400
gaagcaagcc cttatgtcgg agctgaagat catgagtcac cttgggcccc acctgaacgt    2460
ggtcaacctg ttgggggcct gcaccaaagg aggacccatc tatatcatca ctgagtactg    2520
ccgctacgga gacctggtgg actacctgca ccgcaacaaa cacaccttcc tgcagcacca    2580
ctccgacaag cgccgcccgc ccagcgcgga gctctacagc aatgctctgc ccgttgggct    2640 cccccctgccc agccatgtgt ccttgaccgg ggagagcgac ggtggctaca tggacatgag    2700
caaggacgag tcggtggact atgtgcccat gctggacatg aaaggagacg tcaaatatgc    2760
agacatcgag tcctccaact acatggcccc ttacgataac tacgttccct ctgcccctga    2820
gaggacctgc cgagcaactt tgatcaacga gtctccagtg ctaagctaca tggacctcgt    2880
gggcttcagc taccaggtgg ccaatggcat ggagtttctg gcctccaaga actgcgtcca    2940
cagagacctg gcggctagga acgtgctcat ctgtgaaggc aagctggtca agatctgtga    3000
ctttggcctg gctcgagaca tcatgcggga ctcgaattac atctccaaag gcagcacctt    3060 tttgcctttta aagtggatgg ctccggagag catcttcaac agcctctaca ccaccctgag    3120
cgacgtgtgg tccttcggga tcctgctctg ggagatcttc accttgggtg caccccctta    3180
cccagagctg cccatgaacg agcagttcta caatgccatc aaacgggtt accgcatggc    3240 ccagcctgcc catgcctccg acgagatcta tgagatcatg cagaagtgct gggaagagaa    3300
gtttgagatt cggccccccct ctcccagct ggtgctgctt ctcgagagac tgttgggcga    3360
aggttacaaa aagaagtacc agcaggtgga tgaggagttt ctgaggagtg accacccagc    3420
catccttcgg tccaggcccc gcttgcctgg gttccatggc ctccgatctc ccctggacac    3480
cagctccgtc ctctatactg ccgtgcagcc caatgagggt gacaacgact atatcatccc    3540
cctgcctgac cccaaacccg aggttgctga cgagggccca ctggagggtt cccccagcct    3600
```

| | |
|---|---|
| agccagctcc accctgaatg aagtcaacac ctcctcaacc atctcctgtg acagccccct | 3660 |
| ggagccccag gacgaaccag agccagagcc ccagcttgag ctccaggtgg agccggagcc | 3720 |
| agagctggaa cagttgccgg attcggggtg ccctgcgcct cgggcggaag cagaggatag | 3780 |
| cttcctgtag ggggctggcc cctaccctgc cctgcctgaa gctcccccc tgccagcacc | 3840 |
| cagcatctcc tggcctggcc tgaccgggct tcctgtcagc caggctgccc ttatcagctg | 3900 |
| tccccttctg gaagctttct gctcctgacg tgttgtgccc caaaccctgg ggctggctta | 3960 |
| ggaggcaaga aaactgcagg ggccgtgacc agccctctgc ctccagggag gccaactgac | 4020 |
| tctgagccag ggttccccca gggaactcag ttttcccata tgtaagatgg aaagttagg | 4080 |
| cttgatgacc cagaatctag gattctctcc ctggctgaca ggtggggaga ccgaatccct | 4140 |
| ccctgggaag attcttggag ttactgaggt ggtaaattaa cttttttctg ttcagccagc | 4200 |
| taccccctaa ggaatcatag ctctctcctc gcactttat ccacccagga gctagggaag | 4260 |
| agaccctagc ctccctggct gctggctgag ctagggccta gccttgagca gtgttgcctc | 4320 |
| atccagaaga aagccagtct cctccctatg atgccagtcc ctgcgttccc tggcccgagc | 4380 |
| tggtctgggg ccattaggca gcctaattaa tgctggaggc tgagccaagt acaggacacc | 4440 |
| cccagcctgc agcccttgcc cagggcactt ggagcacacg cagccatagc aagtgcctgt | 4500 |
| gtccctgtcc ttcaggccca tcagtcctgg ggcttttttct ttatcaccct cagtcttaat | 4560 |
| ccatccacca gagtctagaa ggccagacgg ccccgcatc tgtgatgaga atgtaaatgt | 4620 |
| gccagtgtgg agtggccacg tgtgtgtgcc agtatatggc cctggctctg cattggacct | 4680 |
| gctatgaggc tttggaggaa tccctcaccc tctctgggcc tcagtttccc cttcaaaaaa | 4740 |
| tgaataagtc ggacttatta actctgagtg ccttgccagc actaacattc tagagtattc | 4800 |
| caggtggttg cacatttgtc cagatgaagc aaggccatat accctaaact tccatcctgg | 4860 |
| gggtcagctg ggctcctggg agattccaga tcacacatca cactctgggg actcaggaac | 4920 |
| catgcccctt ccccaggccc ccagcaagtc tcaagaacac agctgcacag gccttgactt | 4980 |
| agagtgacag ccggtgtcct ggaaagcccc cagcagctgc cccagggaca tgggaagacc | 5040 |
| acgggacctc tttcactacc cacgatgacc tccgggggta tcctgggcaa aagggacaaa | 5100 |
| gagggcaaat gagatcacct cctgcagccc accactccag cacctgtgcc gaggtctgcg | 5160 |
| tcgaagacag aatggacagt gaggacagtt atgtcttgta aaagacaaga agcttcagat | 5220 |
| gggtacccca agaaggatgt gagaggtggg cgctttggag gtttgcccct cacccaccag | 5280 |
| ctgccccatc cctgaggcag cgctccatgg gggtatggtt ttgtcactgc ccagacctag | 5340 |
| cagtgacatc tcattgtccc cagcccagtg ggcattggag gtgccagggg agtcagggtt | 5400 |
| gtagccaaga cgcccccgca cggggagggt tgggaagggg gtgcaggaag ctcaacccct | 5460 |
| ctgggcacca accctgcatt gcaggttggc accttacttc cctgggatcc ccagagttgg | 5520 |
| tccaaggagg gagagtgggt tctcaatacg gtaccaaaga tataatcacc taggtttaca | 5580 |
| aatattttta ggactcacgt taactcacat ttatacagca gaaatgctat tttgtatgct | 5640 |
| gttaagtttt tctatctgtg tactttttt taagggaaag atttaatat taaacctggt | 5700 |
| gcttctcact cacaaaaa | 5718 |

<210> SEQ ID NO 2
<211> LENGTH: 1106
<212> TYPE: PRT
<213> ORGANISM: Homo sapiens

```
<400> SEQUENCE: 2

Met Arg Leu Pro Gly Ala Met Pro Ala Leu Ala Leu Lys Gly Glu Leu
1               5                   10                  15

Leu Leu Leu Ser Leu Leu Leu Leu Glu Pro Gln Ile Ser Gln Gly
                20                  25                  30

Leu Val Val Thr Pro Pro Gly Pro Glu Leu Val Leu Asn Val Ser Ser
                35                  40                  45

Thr Phe Val Leu Thr Cys Ser Gly Ser Ala Pro Val Val Trp Glu Arg
50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
                100                 105                 110

Arg Lys Arg Leu Tyr Ile Phe Val Pro Asp Pro Thr Val Gly Phe Leu
                115                 120                 125

Pro Asn Asp Ala Glu Glu Leu Phe Ile Phe Leu Thr Glu Ile Thr Glu
                130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
                180                 185                 190

Thr Ile Gly Asp Arg Glu Val Asp Ser Asp Ala Tyr Tyr Val Tyr Arg
                195                 200                 205

Leu Gln Val Ser Ser Ile Asn Val Ser Val Asn Ala Val Gln Thr Val
                210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
                260                 265                 270

Arg Ser Ile Leu His Ile Pro Ser Ala Glu Leu Glu Asp Ser Gly Thr
                275                 280                 285

Tyr Thr Cys Asn Val Thr Glu Ser Val Asn Asp His Gln Asp Glu Lys
                290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
                340                 345                 350

Asp Asn Arg Thr Leu Gly Asp Ser Ser Ala Gly Glu Ile Ala Leu Ser
                355                 360                 365

Thr Arg Asn Val Ser Glu Thr Arg Tyr Val Ser Glu Leu Thr Leu Val
                370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415
```

-continued

Val Arg Val Leu Glu Leu Ser Glu Ser His Pro Asp Ser Gly Glu Gln
            420                 425                 430

Thr Val Arg Cys Arg Gly Arg Gly Met Pro Gln Pro Asn Ile Ile Trp
            435                 440                 445

Ser Ala Cys Arg Asp Leu Lys Arg Cys Pro Arg Glu Leu Pro Pro Thr
450                 455                 460

Leu Leu Gly Asn Ser Ser Glu Glu Ser Gln Leu Glu Thr Asn Val
465                 470                 475                 480

Thr Tyr Trp Glu Glu Gln Glu Phe Glu Val Val Ser Thr Leu Arg
                485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
            515                 520                 525

Pro Phe Lys Val Val Val Ile Ser Ala Ile Leu Ala Leu Val Val Leu
            530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
                565                 570                 575

His Glu Tyr Ile Tyr Val Asp Pro Met Gln Leu Pro Tyr Asp Ser Thr
            580                 585                 590

Trp Glu Leu Pro Arg Asp Gln Leu Val Leu Gly Arg Thr Leu Gly Ser
            595                 600                 605

Gly Ala Phe Gly Gln Val Val Glu Ala Thr Ala His Gly Leu Ser His
            610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
                645                 650                 655

His Leu Gly Pro His Leu Asn Val Val Asn Leu Leu Gly Ala Cys Thr
            660                 665                 670

Lys Gly Gly Pro Ile Tyr Ile Ile Thr Glu Tyr Cys Arg Tyr Gly Asp
            675                 680                 685

Leu Val Asp Tyr Leu His Arg Asn Lys His Thr Phe Leu Gln His His
            690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
                725                 730                 735

Asp Gly Gly Tyr Met Asp Met Ser Lys Asp Glu Ser Val Asp Tyr Val
            740                 745                 750

Pro Met Leu Asp Met Lys Gly Asp Val Lys Tyr Ala Asp Ile Glu Ser
            755                 760                 765

Ser Asn Tyr Met Ala Pro Tyr Asp Asn Tyr Val Pro Ser Ala Pro Glu
770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
                805                 810                 815

Leu Ala Ser Lys Asn Cys Val His Arg Asp Leu Ala Ala Arg Asn Val
            820                 825                 830

```
Leu Ile Cys Glu Gly Lys Leu Lys Ile Cys Asp Phe Gly Leu Ala
        835                 840                 845
Arg Asp Ile Met Arg Asp Ser Asn Tyr Ile Ser Lys Gly Ser Thr Phe
850                 855                 860
Leu Pro Leu Lys Trp Met Ala Pro Glu Ser Ile Phe Asn Ser Leu Tyr
865                 870                 875                 880
Thr Thr Leu Ser Asp Val Trp Ser Phe Gly Ile Leu Leu Trp Glu Ile
                885                 890                 895
Phe Thr Leu Gly Gly Thr Pro Tyr Pro Glu Leu Pro Met Asn Glu Gln
                900                 905                 910
Phe Tyr Asn Ala Ile Lys Arg Gly Tyr Arg Met Ala Gln Pro Ala His
                915                 920                 925
Ala Ser Asp Glu Ile Tyr Glu Ile Met Gln Lys Cys Trp Glu Glu Lys
        930                 935                 940
Phe Glu Ile Arg Pro Pro Phe Ser Gln Leu Val Leu Leu Leu Glu Arg
945                 950                 955                 960
Leu Leu Gly Glu Gly Tyr Lys Lys Lys Tyr Gln Gln Val Asp Glu Glu
                965                 970                 975
Phe Leu Arg Ser Asp His Pro Ala Ile Leu Arg Ser Gln Ala Arg Leu
                980                 985                 990
Pro Gly Phe His Gly Leu Arg Ser Pro Leu Asp Thr Ser Ser Val Leu
        995                 1000                1005
Tyr Thr Ala Val Gln Pro Asn Glu Gly Asp Asn Asp Tyr Ile Ile
        1010                1015                1020
Pro Leu Pro Asp Pro Lys Pro Glu Val Ala Asp Glu Gly Pro Leu
        1025                1030                1035
Glu Gly Ser Pro Ser Leu Ala Ser Ser Thr Leu Asn Glu Val Asn
        1040                1045                1050
Thr Ser Ser Thr Ile Ser Cys Asp Ser Pro Leu Glu Pro Gln Asp
        1055                1060                1065
Glu Pro Glu Pro Glu Pro Gln Leu Glu Leu Gln Val Glu Pro Glu
        1070                1075                1080
Pro Glu Leu Glu Gln Leu Pro Asp Ser Gly Cys Pro Ala Pro Arg
        1085                1090                1095
Ala Glu Ala Glu Asp Ser Phe Leu
        1100                1105

<210> SEQ ID NO 3
<211> LENGTH: 8089
<212> TYPE: DNA
<213> ORGANISM: Homo sapiens

<400> SEQUENCE: 3
gcggcgcgga ggctggcccg ggacgcgccc ggagcccagg gaaggaggga ggaggggagg     60
gtcgcggccg gccgccatgg ggccggggc ccgtggccgc cgccgccgcc gtcgcccgat    120
gtcgccgcca ccgccaccgc cacccgtgcg ggcgctgccc ctgctgctgc tgctagcggg    180
gccgggggct gcagcccccc cttgcctgga cggaagcccg tgtgcaaatg gaggtcgttg    240
cacccagctg ccctcccggg aggctgcctg cctgtgcccg cctggctggg tgggtgagcg    300
gtgtcagctg gaggacccct gtcactcagg cccctgtgct ggccgtggtg tctgccagag    360
ttcagtggtg gctggcaccg cccgattctc atgccggtgc cccgtggct tccgaggccc    420
tgactgctcc ctgccagatc cctgcctcag cagcccttgt gccacggtg cccgctgctc    480
agtggggccc gatggacgct tcctctgctc ctgcccacct ggctaccagg ccgcagctg     540
```

```
ccgaagcgac gtggatgagt gccgggtggg tgagccctgc cgccatggtg gcacctgcct    600
caacacacct ggctccttcc gctgccagtg tccagctggc tacacagggc cactatgtga    660
gaaccccgcg gtgccctgtg caccctcacc atgccgtaac gggggcacct gcaggcagag    720
tggcgacctc acttacgact gtgcctgtct cctgggtttt gagggtcaga attgtgaagt    780
gaacgtggac gactgtccag gacaccgatg tctcaatggg gggacatgcg tggatggcgt    840
caacacctat aactgccagt gccctcctga gtggacaggc cagttctgca cggaggacgt    900
ggatgagtgt cagctgcagc ccaacgcctg ccacaatggg ggtacctgct tcaacacgct    960
gggtggccac agctgcgtgt gtgtcaatgg ctggacaggc gagagctgca gtcagaatat   1020
cgatgactgt gccacagccg tgtgcttcca tggggccacc tgccatgacc gcgtggcttc   1080
tttctactgt gcctgcccca tgggcaagac tggcctcctg tgtcacctgg atgacgcctg   1140
tgtcagcaac ccctgccacg aggatgctat ctgtgacaca aatccggtga acggccgggc   1200
catttgcacc tgtcctcccg gcttcacggg tggggcatgt gaccaggatg tggacgagtg   1260
ctctatcggc gccaacccct gcgagcactt gggcaggtgc gtgaacacgc agggctcctt   1320
cctgtgccag tgcggtcgtg gctacactgg acctcgctgt gagaccgatg tcaacgagtg   1380
tctgtcgggg ccctgccgaa accaggccac gtgcctcgac cgcataggcc agttcacctg   1440
tatctgtatg gcaggcttca caggaaccta ttgcgaggtg gacattgacg agtgtcagag   1500
tagcccctgt gtcaacggtg gggtctgcaa ggaccgagtc aatggcttca gctgcacctg   1560
cccctcgggc ttcagcggct ccacgtgtca gctggacgtg gacgaatgcg ccagcacgcc   1620
ctgcaggaat ggcgccaaat gcgtggacca gcccgatggc tacgagtgcc gctgtgccga   1680
gggctttgag ggcacgctgt gtgatcgcaa cgtggacgac tgctcccctg acccatgcca   1740
ccatggtcgc tgcgtggatg gcatcgccag cttctcatgt gcctgtgctc ctggctacac   1800
gggcacacgc tgcgagagcc aggtggacga atgccgcagc cagccctgcc gccatggcgg   1860
caaatgccta gacctggtgg acaagtacct ctgccgctgc cttctgggga ccacaggtgt   1920
gaactgcgaa gtgaacattg acgactgtgc cagcaacccc tgcacctttg gagtctgccg   1980
tgatggcatc aaccgctacg actgtgtctg ccaacctggc ttcacagggc ccttttgtaa   2040
cgtggagatc aatgagtgtg cttccagccc atgcggcgag ggaggttcct gtgtggatgg   2100
ggaaaatggc ttccgctgcc tctgcccgcc tggctccttg ccccccactct gcctccccc   2160
gagccatccc tgtgcccatg agccctgcag tcacggcatc tgctatgatg cacctggcgg   2220
gttccgctgt gtgtgtgagc ctggctggag tggccccgc tgcagccaga gcctggcccg   2280
agacgcctgt gagtcccagc cgtgcagggc cggtgggaca tgcagcagcg atggaatggg   2340
tttccactgc acctgcccgc ctggtgtcca gggacgtcag tgtgaactcc tctccccctg   2400
caccccgaac cctgtgagc atgggggccg ctgcgagtct gcccctggcc agctgcctgt   2460
ctgctcctgc ccccagggct ggcaaggcc acgatgccag caggatgtgg acgagtgtgc   2520
tggccccgca ccctgtggcc ctcatggtat ctgcaccaac ctggcaggga gtttcagctg   2580
cacctgccat ggagggtaca ctggcccttc ctgcgatcag gacatcaatg actgtgaccc   2640
caacccatgc tgaacggtg gctcgtgcca agacggcgtg ggctcctttt cctgctcctg   2700
cctccctggt ttcgccggcc cacgatgcgc ccgcgatgtg gatgagtgcc tgagcaaccc   2760
ctgcggcccg gcacctgta ccgaccacgt ggcctccttc acctgcacct gcccgccagg   2820
ctacggaggc ttccactgcg aacaggacct gcccgactgc agcccagct cctgcttcaa   2880
tggcgggacc tgtgtggacg gcgtgaactc gttcagctgc ctgtgccgtc ccggctacac   2940
```

```
aggagcccac tgccaacatg aggcagaccc ctgcctctcg cggccctgcc tacacggggg      3000
cgtctgcagc gccgcccacc ctggcttccg ctgcacctgc ctcgagagct tcacgggccc      3060
gcagtgccag acgctggtgg attggtgcag ccgccagcct tgtcaaaacg ggggtcgctg      3120
cgtccagact ggggcctatt gcctttgtcc ccctggatgg agcggacgcc tctgtgacat      3180
ccgaagcttg ccctgcaggg aggccgcagc ccagatcggg gtgcggctgg agcagctgtg      3240
tcaggcgggt gggcagtgtg tggatgaaga cagctcccac tactgcgtgt gcccagaggg      3300
ccgtactggt agccactgtg agcaggaggt ggacccctgc ttggcccagc cctgccagca      3360 tgggggacc tgccgtggct atatggggg ctacatgtgt gagtgtcttc ctggctacaa         3420
tggtgataac tgtgaggacg acgtggacga gtgtgcctcc cagccctgcc agcacggggg      3480
ttcatgcatt gacctcgtgg cccgctatct ctgctcctgt cccccaggaa cgctgggggt      3540
gctctgcgag attaatgagg atgactgcgg cccaggccca ccgctggact cagggccccg      3600
gtgcctacac aatggcacct gcgtggacct ggtgggtggt ttccgctgca cctgtccccc      3660
aggatacact ggtttgcgct gcgaggcaga catcaatgag tgtcgctcag gtgcctgcca      3720
cgcggcacac acccgggact gcctgcagga cccaggcgga ggtttccgtt gcctttgtca      3780
tgctggcttc tcaggtcctc gctgtcagac tgtcctgtct ccctgcgagt cccagccatg      3840
ccagcatgga ggccagtgcc gtcctagccc gggtcctggg ggtgggctga ccttcacctg      3900
tcactgtgcc cagccgttct gggtccgcg ttgcgagcgg gtggcgcgct cctgccggga       3960
gctgcagtgc ccggtgggcg tcccatgcca gcagacgccc cgcgggccgc gctgcgcctg      4020 cccccaggg ttgtcgggac cctcctgccg cagcttcccg gggtcgccgc cggggggcag       4080
caacgccagc tgcgcggccg cccctgtct ccacgggggc tcctgccgcc ccgcgccgct       4140
cgcgcccttc ttccgctgcg cttgcgcgca gggctggacc gggccgcgct gcgaggcgcc      4200
cgccgcggca cccgaggtct cggaggagcc gcggtgcccg cgcgccgcct gccaggccaa      4260
gcgcggggac cagcgctgcg accgcgagtg caacagccca ggctgcggct gggacggcgg      4320
cgactgctcg ctgagcgtgg gcgaccctg gcggcaatgc gaggcgctgc agtgctggcg        4380
cctcttcaac aacagccgct gcgaccccgc ctgcagctcg cccgcctgcc tctacgacaa      4440
cttcgactgc cacgccggtg gccgcgagcg cacttgcaac ccggtgtacg agaagtactg      4500
cgccgaccac tttgccgacg gccgctgcga ccagggctgc aacacggagg agtgcggctg      4560
ggatgggctg gattgtgcca gcgaggtgcc ggccctgctg gcccgcggcg tgctggtgct      4620
cacagtgctg ctgccgccag aggagctact gcgttccagc gccgactttc tgcagcggct      4680
cagcgccatc ctgcgcacct cgctgcgctt ccgcctggac gcgcacggcc aggccatggt      4740
cttcccttac caccggccta gtcctggctc cgaaccccgg gcccgtcggg agctggcccc      4800
cgaggtgatc ggctcggtag taatgctgga gattgacaac cggctctgcc tgcagtcgcc      4860
tgagaatgat cactgcttcc ccgatgccca gagcgccgct gactacctgg agcgttgtc       4920 agcggtggag cgcctggact tcccgtaccc actgcgggac gtgcgggggg agccgctgga      4980
gcctccagaa cccagcgtcc cgctgctgcc actgctagtg gcgggcgctg tcttgctgct      5040
ggtcattctc gtcctgggtg tcatggtggc ccggcgcaag cgcgagcaca gcaccctctg      5100
gttccctgag ggcttctcac tgcacaagga cgtggcctct ggtcacaagg gccggcggga      5160
acccgtgggc caggacgcgc tgggcatgaa gaacatggcc aagggtgaga gcctgatggg      5220 ggaggtggc acagactgga tggacacaga gtgcccagag gccaagcggc taaaggtaga       5280
ggagccaggc atgggggctg aggaggctgt ggattgccgt cagtggactc aacaccatct      5340
```

```
ggttgctgct gacatccgcg tggcaccagc catggcactg acaccaccac agggcgacgc    5400
agatgctgat ggcatggatg tcaatgtgcg tggcccagat ggcttcaccc cgctaatgct    5460
ggcttccttc tgtgggggg ctctggagcc aatgccaact gaagaggatg aggcagatga     5520
cacatcagct agcatcatct ccgacctgat ctgccagggg gctcagcttg ggcacggac     5580 tgaccgtact ggcgagactg cttttgcacct ggctgcccgt tatgcccgtg ctgatgcagc   5640
caagcggctg ctggatgctg gggcagacac caatgcccag gaccactcag ccgcactcc    5700 cctgcacaca gctgtcacag ccgatgccca gggtgtcttc cagattctca tccgaaaccg    5760
ctctacagac ttggatgccc gcatggcaga tggctcaacg gcactgatcc tggcggcccg    5820
cctggcagta gagggcatgg tggaagagct catcgccagc catgctgatg tcaatgctgt    5880
ggatgagctt gggaaatcag ccttacactg gctgcggct gtgaacaacg tggaagccac     5940
tttggccctg ctcaaaaatg gagccaataa ggacatgcag gatagcaagg aggagacccc    6000
cctattcctg gccgcccgcg agggcagcta tgaggctgcc aagctgctgt tggaccactt    6060
tgccaaccgt gagatcaccg accacctgga caggctgccg cgggacgtag cccaggagag    6120
actgcaccag gacatcgtgc gcttgctgga tcaacccagt gggcccccgca gccccccgg    6180 tccccacggc ctggggcctc tgctctgtcc tccaggggcc ttcctccctg gcctcaaagc    6240
ggcacagtcg gggtccaaga agagcaggag gcccccgggg aaggcggggc tggggccgca    6300
gggcccccgg gggcggggca agaagctgac gctggcctgc ccgggccccc tggctgacag    6360
ctcggtcacg ctgtcgcccg tggactcgct ggactcccg cggcctttcg gtgggccccc     6420
tgcttcccct ggtggcttcc cccttgaggg gccctatgca gctgccactg ccactgcagt    6480
gtctctggca cagcttggtg gcccaggccg ggcgggtcta gggcgccagc cccctggagg    6540
atgtgtactc agcctgggcc tgctgaaccc tgtggctgtg cccctcgatt gggcccggct    6600
gcccccacct gcccctccag gcccctcgtt cctgctgcca ctggcgccgg accccagct    6660 gctcaaccca gggaccccg tctccccgca ggagcggccc ccgccttacc tggcagtccc    6720
aggacatggc gaggagtacc cggcggctgg ggcacacagc agcccccca aggcccgctt    6780 cctgcgggtt cccagtgagc acccttacct gaccccatcc cccgaatccc ctgagcactg    6840
ggccagcccc tcacctccct ccctctcaga ctggtccgaa tccacgccta gcccagccac    6900
tgccactggg gccatggcca ccaccactgg ggcactgcct gcccagccac ttccccttgtc   6960 tgttcccagc tcccttgctc aggcccagac ccagctgggg cccccagccgg aagttacccc    7020 caagaggcaa gtgttggcct gagacgctcg tcagttctta gatcttgggg gcctaaagag    7080
acccccgtcc tgcctccttt cttttctctgt ctcttccttc cttttagtct ttttcatcct    7140
cttctctttc caccaaccct cctgcatcct tgccttgcag cgtgaccgag ataggtcatc    7200
agcccagggc ttcagtcttc ctttatttat aatgggtggg ggctaccacc caccctctca    7260
gtcttgtgaa gagtctggga cctccttctt ccccacttct ctcttccctc attcctttct    7320
ctctccttct ggcctctcat ttccttacac tctgacatga atgaattatt attattttta    7380
tttttctttt tttttttaca ttttgtatag aaacaaattc atttaaacaa acttattatt    7440
attatttttt acaaaatata tatatggaga tgctccctcc cctgtgaac ccccagtgc      7500 ccccgtgggg ctgagtctgt gggcccattc ggccaagctg gattctgtgt acctagtaca    7560
caggcatgac tgggatcccg tgtaccgagt acacgaccca ggtatgtacc aagtaggcac    7620
ccttgggcgc acccactggg gccaggggtc ggggagtgt tggagcctc ctccccaccc      7680 cacctccctc acttcactgc attccagatg ggacatgttc catagccttg ctggggaagg    7740
```

-continued

```
gcccactgcc aactccctct gccccagccc caccttggc catctccctt tgggaactag    7800
ggggctgctg gtgggaaatg ggagccaggg cagatgtatg cattcctttg tgtccctgta    7860
aatgtgggac tacaagaaga ggagctgcct gagtggtact ttctcttcct ggtaatcctc    7920
tggcccagcc tcatggcaga atagaggtat ttttaggcta tttttgtaat atggcttctg    7980
gtcaaaatcc ctgtgtagct gaattcccaa gccctgcatt gtacagcccc ccactcccct    8040
caccacctaa taaggaata gttaacactc aaaaaaaaaa aaaaaaaa                  8089
```

<210> SEQ ID NO 4
<211> LENGTH: 2321
<212> TYPE: PRT
<213> ORGANISM: Homo sapiens

<400> SEQUENCE: 4

```
Met Gly Pro Gly Ala Arg Gly Arg Arg Arg Arg Pro Met Ser
1               5                   10                  15

Pro Pro Pro Pro Pro Pro Val Arg Ala Leu Pro Leu Leu Leu Leu
                20                  25                  30

Leu Ala Gly Pro Gly Ala Ala Ala Pro Pro Cys Leu Asp Gly Ser Pro
        35                  40                  45

Cys Ala Asn Gly Gly Arg Cys Thr Gln Leu Pro Ser Arg Glu Ala Ala
    50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95

Val Val Ala Gly Thr Ala Arg Phe Ser Cys Arg Cys Pro Arg Gly Phe
            100                 105                 110

Arg Gly Pro Asp Cys Ser Leu Pro Asp Pro Cys Leu Ser Ser Pro Cys
        115                 120                 125

Ala His Gly Ala Arg Cys Ser Val Gly Pro Asp Gly Arg Phe Leu Cys
    130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                165                 170                 175

Thr Pro Gly Ser Phe Arg Cys Gln Cys Pro Ala Gly Tyr Thr Gly Pro
            180                 185                 190

Leu Cys Glu Asn Pro Ala Val Pro Cys Ala Pro Ser Pro Cys Arg Asn
        195                 200                 205

Gly Gly Thr Cys Arg Gln Ser Gly Asp Leu Thr Tyr Asp Cys Ala Cys
    210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
                245                 250                 255

Thr Tyr Asn Cys Gln Cys Pro Pro Glu Trp Thr Gly Gln Phe Cys Thr
            260                 265                 270

Glu Asp Val Asp Glu Cys Gln Leu Gln Pro Asn Ala Cys His Asn Gly
        275                 280                 285

Gly Thr Cys Phe Asn Thr Leu Gly Gly His Ser Cys Val Cys Val Asn
    290                 295                 300

Gly Trp Thr Gly Glu Ser Cys Ser Gln Asn Ile Asp Asp Cys Ala Thr
305                 310                 315                 320
```

-continued

Ala Val Cys Phe His Gly Ala Thr Cys His Asp Arg Val Ala Ser Phe
            325                 330                 335

Tyr Cys Ala Cys Pro Met Gly Lys Thr Gly Leu Leu Cys His Leu Asp
            340                 345                 350

Asp Ala Cys Val Ser Asn Pro Cys His Glu Asp Ala Ile Cys Asp Thr
            355                 360                 365

Asn Pro Val Asn Gly Arg Ala Ile Cys Thr Cys Pro Pro Gly Phe Thr
370                 375                 380

Gly Gly Ala Cys Asp Gln Asp Val Asp Glu Cys Ser Ile Gly Ala Asn
385                 390                 395                 400

Pro Cys Glu His Leu Gly Arg Cys Val Asn Thr Gln Gly Ser Phe Leu
            405                 410                 415

Cys Gln Cys Gly Arg Gly Tyr Thr Gly Pro Arg Cys Glu Thr Asp Val
            420                 425                 430

Asn Glu Cys Leu Ser Gly Pro Cys Arg Asn Gln Ala Thr Cys Leu Asp
            435                 440                 445

Arg Ile Gly Gln Phe Thr Cys Ile Cys Met Ala Gly Phe Thr Gly Thr
            450                 455                 460

Tyr Cys Glu Val Asp Ile Asp Glu Cys Gln Ser Ser Pro Cys Val Asn
465                 470                 475                 480

Gly Gly Val Cys Lys Asp Arg Val Asn Gly Phe Ser Cys Thr Cys Pro
            485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
            515                 520                 525

Tyr Glu Cys Arg Cys Ala Glu Gly Phe Glu Gly Thr Leu Cys Asp Arg
            530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
            565                 570                 575

Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
            595                 600                 605

Pro Ser Gly Thr Thr Gly Val Asn Cys Glu Val Asn Ile Asp Asp Cys
            610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
            645                 650                 655

Glu Ile Asn Glu Cys Ala Ser Ser Pro Cys Gly Glu Gly Gly Ser Cys
            660                 665                 670

Val Asp Gly Glu Asn Gly Phe Arg Cys Leu Cys Pro Pro Gly Ser Leu
            675                 680                 685

Pro Pro Leu Cys Leu Pro Pro Ser His Pro Cys Ala His Glu Pro Cys
            690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
            725                 730                 735

```
Ala Cys Glu Ser Gln Pro Cys Arg Ala Gly Gly Thr Cys Ser Ser Asp
            740                 745                 750
Gly Met Gly Phe His Cys Thr Cys Pro Pro Gly Val Gln Gly Arg Gln
        755                 760                 765
Cys Glu Leu Leu Ser Pro Cys Thr Pro Asn Pro Cys Glu His Gly Gly
    770                 775                 780
Arg Cys Glu Ser Ala Pro Gly Gln Leu Pro Val Cys Ser Cys Pro Gln
785                 790                 795                 800
Gly Trp Gln Gly Pro Arg Cys Gln Asp Val Asp Glu Cys Ala Gly
                805                 810                 815
Pro Ala Pro Cys Gly Pro His Gly Ile Cys Thr Asn Leu Ala Gly Ser
            820                 825                 830
Phe Ser Cys Thr Cys His Gly Gly Tyr Thr Gly Pro Ser Cys Asp Gln
        835                 840                 845
Asp Ile Asn Asp Cys Asp Pro Asn Pro Cys Leu Asn Gly Gly Ser Cys
    850                 855                 860
Gln Asp Gly Val Gly Ser Phe Ser Cys Ser Cys Leu Pro Gly Phe Ala
865                 870                 875                 880
Gly Pro Arg Cys Ala Arg Asp Val Asp Glu Cys Leu Ser Asn Pro Cys
                885                 890                 895
Gly Pro Gly Thr Cys Thr Asp His Val Ala Ser Phe Thr Cys Thr Cys
            900                 905                 910
Pro Pro Gly Tyr Gly Gly Phe His Cys Glu Gln Asp Leu Pro Asp Cys
        915                 920                 925
Ser Pro Ser Ser Cys Phe Asn Gly Gly Thr Cys Val Asp Gly Val Asn
    930                 935                 940
Ser Phe Ser Cys Leu Cys Arg Pro Gly Tyr Thr Gly Ala His Cys Gln
945                 950                 955                 960
His Glu Ala Asp Pro Cys Leu Ser Arg Pro Cys Leu His Gly Gly Val
                965                 970                 975
Cys Ser Ala Ala His Pro Gly Phe Arg Cys Thr Cys Leu Glu Ser Phe
            980                 985                 990
Thr Gly Pro Gln Cys Gln Thr Leu  Val Asp Trp Cys Ser Arg Gln Pro
        995                 1000                1005
Cys Gln Asn Gly Gly Arg Cys  Val Gln Thr Gly Ala  Tyr Cys Leu
    1010                1015                1020
Cys Pro Pro Gly Trp Ser Gly Arg Leu Cys Asp Ile  Arg Ser Leu
    1025                1030                1035
Pro Cys Arg Glu Ala Ala Ala  Gln Ile Gly Val Arg  Leu Glu Gln
    1040                1045                1050
Leu Cys  Gln Ala Gly Gly Gln  Cys Val Asp Glu Asp  Ser Ser His
    1055                1060                1065
Tyr Cys  Val Cys Pro Glu Gly Arg Thr Gly Ser His  Cys Glu Gln
    1070                1075                1080
Glu Val Asp Pro Cys Leu Ala  Gln Pro Cys Gln His  Gly Gly Thr
1085                1090                1095
Cys Arg  Gly Tyr Met Gly Gly Tyr Met Cys Glu Cys  Leu Pro Gly
    1100                1105                1110
Tyr Asn  Gly Asp Asn Cys Glu  Asp Asp Val Asp Glu  Cys Ala Ser
        1115                1120                1125
Gln Pro  Cys Gln His Gly Gly  Ser Cys Ile Asp Leu  Val Ala Arg
    1130                1135                1140
```

-continued

Tyr Leu Cys Ser Cys Pro Pro Gly Thr Leu Gly Val Leu Cys Glu
1145                 1150                1155

Ile Asn Glu Asp Asp Cys Gly Pro Gly Pro Pro Leu Asp Ser Gly
1160                 1165                1170

Pro Arg Cys Leu His Asn Gly Thr Cys Val Asp Leu Val Gly Gly
1175                 1180                1185

Phe Arg Cys Thr Cys Pro Pro Gly Tyr Thr Gly Leu Arg Cys Glu
1190                 1195                1200

Ala Asp Ile Asn Glu Cys Arg Ser Gly Ala Cys His Ala Ala His
1205                 1210                1215

Thr Arg Asp Cys Leu Gln Asp Pro Gly Gly Gly Phe Arg Cys Leu
1220                 1225                1230

Cys His Ala Gly Phe Ser Gly Pro Arg Cys Gln Thr Val Leu Ser
1235                 1240                1245

Pro Cys Glu Ser Gln Pro Cys Gln His Gly Gly Gln Cys Arg Pro
1250                 1255                1260

Ser Pro Gly Pro Gly Gly Leu Thr Phe Thr Cys His Cys Ala
1265                 1270                1275

Gln Pro Phe Trp Gly Pro Arg Cys Glu Arg Val Ala Arg Ser Cys
1280                 1285                1290

Arg Glu Leu Gln Cys Pro Val Gly Val Pro Cys Gln Gln Thr Pro
1295                 1300                1305

Arg Gly Pro Arg Cys Ala Cys Pro Pro Gly Leu Ser Gly Pro Ser
1310                 1315                1320

Cys Arg Ser Phe Pro Gly Ser Pro Pro Gly Ala Ser Asn Ala Ser
1325                 1330                1335

Cys Ala Ala Ala Pro Cys Leu His Gly Gly Ser Cys Arg Pro Ala
1340                 1345                1350

Pro Leu Ala Pro Phe Phe Arg Cys Ala Cys Ala Gln Gly Trp Thr
1355                 1360                1365

Gly Pro Arg Cys Glu Ala Pro Ala Ala Ala Pro Glu Val Ser Glu
1370                 1375                1380

Glu Pro Arg Cys Pro Arg Ala Ala Cys Gln Ala Lys Arg Gly Asp
1385                 1390                1395

Gln Arg Cys Asp Arg Glu Cys Asn Ser Pro Gly Cys Gly Trp Asp
1400                 1405                1410

Gly Gly Asp Cys Ser Leu Ser Val Gly Asp Pro Trp Arg Gln Cys
1415                 1420                1425

Glu Ala Leu Gln Cys Trp Arg Leu Phe Asn Asn Ser Arg Cys Asp
1430                 1435                1440

Pro Ala Cys Ser Ser Pro Ala Cys Leu Tyr Asp Asn Phe Asp Cys
1445                 1450                1455

His Ala Gly Gly Arg Glu Arg Thr Cys Asn Pro Val Tyr Glu Lys
1460                 1465                1470

Tyr Cys Ala Asp His Phe Ala Asp Gly Arg Cys Asp Gln Gly Cys
1475                 1480                1485

Asn Thr Glu Glu Cys Gly Trp Asp Gly Leu Asp Cys Ala Ser Glu
1490                 1495                1500

Val Pro Ala Leu Leu Ala Arg Gly Val Leu Val Leu Thr Val Leu
1505                 1510                1515

Leu Pro Pro Glu Glu Leu Leu Arg Ser Ser Ala Asp Phe Leu Gln
1520                 1525                1530

```
Arg Leu Ser Ala Ile Leu Arg Thr Ser Leu Arg Phe Arg Leu Asp
1535                1540                1545

Ala His Gly Gln Ala Met Val Phe Pro Tyr His Arg Pro Ser Pro
1550                1555                1560

Gly Ser Glu Pro Arg Ala Arg Arg Glu Leu Ala Pro Glu Val Ile
1565                1570                1575

Gly Ser Val Val Met Leu Glu Ile Asp Asn Arg Leu Cys Leu Gln
1580                1585                1590

Ser Pro Glu Asn Asp His Cys Phe Pro Asp Ala Gln Ser Ala Ala
1595                1600                1605

Asp Tyr Leu Gly Ala Leu Ser Ala Val Glu Arg Leu Asp Phe Pro
1610                1615                1620

Tyr Pro Leu Arg Asp Val Arg Gly Glu Pro Leu Glu Pro Pro Glu
1625                1630                1635

Pro Ser Val Pro Leu Leu Pro Leu Leu Val Ala Gly Ala Val Leu
1640                1645                1650

Leu Leu Val Ile Leu Val Leu Gly Val Met Val Ala Arg Arg Lys
1655                1660                1665

Arg Glu His Ser Thr Leu Trp Phe Pro Glu Gly Phe Ser Leu His
1670                1675                1680

Lys Asp Val Ala Ser Gly His Lys Gly Arg Arg Glu Pro Val Gly
1685                1690                1695

Gln Asp Ala Leu Gly Met Lys Asn Met Ala Lys Gly Glu Ser Leu
1700                1705                1710

Met Gly Glu Val Ala Thr Asp Trp Met Asp Thr Glu Cys Pro Glu
1715                1720                1725

Ala Lys Arg Leu Lys Val Glu Glu Pro Gly Met Gly Ala Glu Glu
1730                1735                1740

Ala Val Asp Cys Arg Gln Trp Thr Gln His His Leu Val Ala Ala
1745                1750                1755

Asp Ile Arg Val Ala Pro Ala Met Ala Leu Thr Pro Pro Gln Gly
1760                1765                1770

Asp Ala Asp Ala Asp Gly Met Asp Val Asn Val Arg Gly Pro Asp
1775                1780                1785

Gly Phe Thr Pro Leu Met Leu Ala Ser Phe Cys Gly Gly Ala Leu
1790                1795                1800

Glu Pro Met Pro Thr Glu Glu Asp Glu Ala Asp Asp Thr Ser Ala
1805                1810                1815

Ser Ile Ile Ser Asp Leu Ile Cys Gln Gly Ala Gln Leu Gly Ala
1820                1825                1830

Arg Thr Asp Arg Thr Gly Glu Thr Ala Leu His Leu Ala Ala Arg
1835                1840                1845

Tyr Ala Arg Ala Asp Ala Ala Lys Arg Leu Leu Asp Ala Gly Ala
1850                1855                1860

Asp Thr Asn Ala Gln Asp His Ser Gly Arg Thr Pro Leu His Thr
1865                1870                1875

Ala Val Thr Ala Asp Ala Gln Gly Val Phe Gln Ile Leu Ile Arg
1880                1885                1890

Asn Arg Ser Thr Asp Leu Asp Ala Arg Met Ala Asp Gly Ser Thr
1895                1900                1905

Ala Leu Ile Leu Ala Ala Arg Leu Ala Val Glu Gly Met Val Glu
1910                1915                1920
```

-continued

```
Glu Leu Ile Ala Ser His Ala Asp Val Asn Ala Val Asp Glu Leu
1925                1930                1935

Gly Lys Ser Ala Leu His Trp Ala Ala Ala Val Asn Asn Val Glu
1940                1945                1950

Ala Thr Leu Ala Leu Leu Lys Asn Gly Ala Asn Lys Asp Met Gln
1955                1960                1965

Asp Ser Lys Glu Glu Thr Pro Leu Phe Leu Ala Ala Arg Glu Gly
1970                1975                1980

Ser Tyr Glu Ala Ala Lys Leu Leu Leu Asp His Phe Ala Asn Arg
1985                1990                1995

Glu Ile Thr Asp His Leu Asp Arg Leu Pro Arg Asp Val Ala Gln
2000                2005                2010

Glu Arg Leu His Gln Asp Ile Val Arg Leu Leu Asp Gln Pro Ser
2015                2020                2025

Gly Pro Arg Ser Pro Pro Gly Pro His Gly Leu Gly Pro Leu Leu
2030                2035                2040

Cys Pro Pro Gly Ala Phe Leu Pro Gly Leu Lys Ala Ala Gln Ser
2045                2050                2055

Gly Ser Lys Lys Ser Arg Arg Pro Pro Gly Lys Ala Gly Leu Gly
2060                2065                2070

Pro Gln Gly Pro Arg Gly Arg Gly Lys Lys Leu Thr Leu Ala Cys
2075                2080                2085

Pro Gly Pro Leu Ala Asp Ser Ser Val Thr Leu Ser Pro Val Asp
2090                2095                2100

Ser Leu Asp Ser Pro Arg Pro Phe Gly Gly Pro Pro Ala Ser Pro
2105                2110                2115

Gly Gly Phe Pro Leu Glu Gly Pro Tyr Ala Ala Ala Thr Ala Thr
2120                2125                2130

Ala Val Ser Leu Ala Gln Leu Gly Gly Pro Gly Arg Ala Gly Leu
2135                2140                2145

Gly Arg Gln Pro Pro Gly Gly Cys Val Leu Ser Leu Gly Leu Leu
2150                2155                2160

Asn Pro Val Ala Val Pro Leu Asp Trp Ala Arg Leu Pro Pro Pro
2165                2170                2175

Ala Pro Pro Gly Pro Ser Phe Leu Leu Pro Leu Ala Pro Gly Pro
2180                2185                2190

Gln Leu Leu Asn Pro Gly Thr Pro Val Ser Pro Gln Glu Arg Pro
2195                2200                2205

Pro Pro Tyr Leu Ala Val Pro Gly His Gly Glu Glu Tyr Pro Ala
2210                2215                2220

Ala Gly Ala His Ser Ser Pro Pro Lys Ala Arg Phe Leu Arg Val
2225                2230                2235

Pro Ser Glu His Pro Tyr Leu Thr Pro Ser Pro Glu Ser Pro Glu
2240                2245                2250

His Trp Ala Ser Pro Ser Pro Pro Ser Leu Ser Asp Trp Ser Glu
2255                2260                2265

Ser Thr Pro Ser Pro Ala Thr Ala Thr Gly Ala Met Ala Thr Thr
2270                2275                2280

Thr Gly Ala Leu Pro Ala Gln Pro Leu Pro Leu Ser Val Pro Ser
2285                2290                2295
```

-continued

```
Ser Leu Ala Gln Ala Gln Thr Gln Leu Gly Pro Gln Pro Glu Val
2300                2305                2310

Thr Pro Lys Arg Gln Val Leu Ala
    2315                2320
```

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
gtcactcacc cgatcacctc                                                    20

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
agcccggtgt acgagaagta                                                    20

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
ctcccacgtg gagtcatagg                                                    20

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
tgtcctagac ggacgaacct                                                    20

<210> SEQ ID NO 9
<211> LENGTH: 20
<212> TYPE: DNA
<213> ORGANISM: Artificial
<220> FEATURE:
<223> OTHER INFORMATION: Primer

<400> SEQUENCE: 9
cagcaggagt gtgctgttgt                                                    20

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
cggggcagaa gagtcagaat                                                    20